United States Patent [19]
Barker

[11] Patent Number: 5,955,464
[45] Date of Patent: Sep. 21, 1999

[54] 4-ANILINOQUINAZOLINE DERIVATIVES BEARING A HETEROARYL SUBSTITUTED AT THE 6-POSITION AND POSSESSING ANTI-CELL-PROLIFERATION PROPERTIES

[75] Inventor: Andrew John Barker, Macclesfield, United Kingdom

[73] Assignee: Zeneca Limited, London, United Kingdom

[21] Appl. No.: 08/860,088

[22] PCT Filed: Nov. 28, 1995

[86] PCT No.: PCT/GB95/02768

§ 371 Date: May 22, 1997

§ 102(e) Date: May 22, 1997

[87] PCT Pub. No.: WO96/16960

PCT Pub. Date: Jun. 6, 1996

[30] Foreign Application Priority Data

Nov. 30, 1994 [GB] United Kingdom ............... 9424233

[51] Int. Cl.$^6$ ............... A01N 43/54; C07D 401/00; C07D 239/72
[52] U.S. Cl. ............... 514/259; 544/284; 544/293
[58] Field of Search ............... 514/259; 544/284, 544/293

[56] References Cited

U.S. PATENT DOCUMENTS

| | | | |
|---|---|---|---|
| 3,266,990 | 8/1966 | Lutz et al. | 167/65 |
| 4,343,940 | 8/1982 | Kreighbaum et al. | 544/283 |
| 5,373,011 | 12/1994 | Haley | 514/259 |
| 5,411,963 | 5/1995 | Dreikom et al. | 514/259 |
| 5,571,815 | 11/1996 | Schaper et al. | 514/269 |
| 5,747,498 | 5/1998 | Schnur et al. | 514/259 |

FOREIGN PATENT DOCUMENTS

| | | |
|---|---|---|
| 0 326 307 | 2/1989 | European Pat. Off. . |
| 0 326 330 A2 | 8/1989 | European Pat. Off. . |
| 0 520 722 A1 | 12/1992 | European Pat. Off. . |
| 566226 | 10/1993 | European Pat. Off. ............... 544/284 |
| 0 682 027 A1 | 11/1995 | European Pat. Off. . |
| 0 787 722 A1 | 8/1997 | European Pat. Off. . |
| 2 033 894 | 5/1980 | United Kingdom . |
| 2 160 201 | 12/1985 | United Kingdom . |
| WO 97/13760 | 4/1977 | WIPO . |
| WO 97/13771 | 4/1977 | WIPO . |
| WO 92/14716 | 9/1992 | WIPO . |
| WO 95/06648 | 3/1995 | WIPO . |
| WO 95/15758 | 6/1995 | WIPO . |
| WO 95/15952 | 6/1995 | WIPO . |
| WO 95/19169 | 7/1995 | WIPO . |
| WO 95/19774 | 7/1995 | WIPO . |
| WO 95/19970 | 7/1995 | WIPO . |
| WO 95/21613 | 8/1995 | WIPO . |
| WO 95/24190 | 9/1995 | WIPO . |
| WO 96/07657 | 3/1996 | WIPO . |
| WO 96/09294 | 3/1996 | WIPO . |
| WO 96/15118 | 5/1996 | WIPO . |
| WO 96/16960 | 6/1996 | WIPO . |

(List continued on next page.)

OTHER PUBLICATIONS

Nomoto et al., CA 112:21004, 1989.

Rewcastle et al., "Tyrosine Kinase Inhibitors. 5. Synthesis and Structure–Activity Relationships for 4-[(Phenylmethyl)amino]– and 4-(Phenylamino)quinazolines as Potent Adenosine 5'-Triphosphate Binding Site Inhibitors of the Tyrosine Kinase Domain of the Epidermal Growth Factor Receptor," J.Med.Chem. 1995, vol. 38, pp. 3482–3487.

Burke, Jr., "Protein–tyrosine kinase inhibitors," Drugs of the Future 1992, vol. 17(2), pp. 119–131.

Spence, "Inhibitors of Tyrosine Kinase Activity as Anticancer Therapeutics: Recent Developments," Expert Opinion in Therapeutic Patents, Jan. 1993, Patent Update, Anticancers, etc., pp. 3–9, Current Drugs Ltd ISSN 0962–2594,.

Spada et al., Small molecule inhibitors of tyrosine Kinase activity, Exp.Opin.Ther.Patents (1995), 5(8):805–817, Patent Update, Oncologic, Endocrine & Metabolic, Ashley Publications Ltd ISSN 1354–3776.

(List continued on next page.)

Primary Examiner—Mukund J. Shah
Assistant Examiner—Tamthom N. Truong
Attorney, Agent, or Firm—Cushman Darby & Cushman Intellectual Property Group of Pillsbury Madison & Sutro, LLP

[57] ABSTRACT

The invention concerns 4-anilinoquinazoline derivatives of the formula I

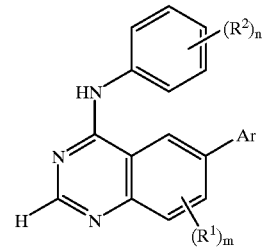

I wherein m is 1 or 2;
  each $R^1$ includes hydrogen, halogeno, (1–4C)alkyl and (1–4C)alkoxy;
  n is 1, 2 or 3;
  each $R^2$ includes hydrogen, hydroxy, halogeno and (1–4C)alkyl; and Ar is a 5- or 9-membered nitrogen-linked heteroaryl moiety containing up to four nitrogen heteroatoms, or Ar is a 5-, 6-, 9- or 10-membered nitrogen-linked unsaturated heterocyclic moiety containing up to three nitrogen heteroatoms which bears one or two substituents selected from oxo and thioxo such as 2-oxo-4-imidazolin-1-yl;
  or a pharmaceutically-acceptable salt thereof;
processes for their preparation, pharmaceutical compositions containing them, and the use of the receptor tyrosine kinase inhibitory properties of the compounds in the treatment of proliferative disease such as cancer.

10 Claims, No Drawings

FOREIGN PATENT DOCUMENTS

| | | |
|---|---|---|
| WO 96/29331 | 9/1996 | WIPO . |
| WO 96/30347 | 10/1996 | WIPO . |
| WO 96/31510 | 10/1996 | WIPO . |
| WO 96/33977 | 10/1996 | WIPO . |
| WO 96/33978 | 10/1996 | WIPO . |
| WO 96/33979 | 10/1996 | WIPO . |
| WO 96/33980 | 10/1996 | WIPO . |
| WO 96/33981 | 10/1996 | WIPO . |
| WO 96/34867 | 11/1996 | WIPO . |
| WO 96/35689 | 11/1996 | WIPO . |
| WO 96/39145 | 12/1996 | WIPO . |
| WO 96/40142 | 12/1996 | WIPO . |
| WO 96/40648 | 12/1996 | WIPO . |
| WO 97/02266 | 1/1997 | WIPO . |
| WO 97/03069 | 1/1997 | WIPO . |
| WO 97/18212 | 5/1997 | WIPO . |

OTHER PUBLICATIONS

Bridges, "The current status of tyrosine kinase inhibitors: do the diarylamine inhibitors of the EGF receptor represent a new beginning?," Exp.Opin.Ther.Patents (1995), 5(12):1245–1257, Editorial Oncologic, Endocrine & Metabolic, 1995 Ashley Publications Ltd ISSN 1354–3776.

Traxler et al., "Recent advances in protein tyrosine kinase inhibitors," Drugs of the Future 1995, vol. 20(12,pp. 1261–1274.

Iyer et al., "Studies in Potential Amoebicides: Part III–Synthesis of $_4$–Substituted Amino–8–Hydroxy) Quinazolines & $_3$–Substituted 8–Hydroxy(&8–Methoxy)–$_4$–Quinazolones," J.Sci.Indust.Res., vol. 15C, Jan. 1956, pp. 1–7.

Kobayashi, Derwent Abstract 82–87007, vol. 6, No. 244, Dec. 1982, JP 57–144266, Sep. 1982, "4–Anilinoquinazoline Derivative, its Preparation and Analgesic and Antiphlogistic Agent Containing Said Derivative as Active Component".

Sankyo and Ube, Derwent Abstract 81–28290, JP 56–20577, Feb. 1981, "4–(N–alkyl:anilino) quinazoline derivs . . . having analgesic and antiinflammatory actions".

Kyorin, Derwent Abstract 84–53835, JP 59–13765, Jan. 1984, "2–(4–Quinazolinyl)amino benzoic acid derivs . . . having analgesic and antiinflammatory activities".

Li et al., Chem.Abs., vol. 92:76445u, 1980, p.674–675.

Lin et al., Chem.Abs., vol. 96:122728w, 1982, p. 695.

Buchdunger et al., "4,5–Dianilinophthalimide: A protein–tyrosine kinase inhibitor with selectivity for the epidermal growth factor receptor signal transduction pathway and potent in vivo antitumor activity," Proc.Natl.Acad.Sci., USA, vol. 91, pp. 2334–2338, Mar. 1994, Applied Biological Sciences.

Trinks et al., "Dianilinophthalimides: Potent and Selective, ATP–Competitive Inhibitors of the EGF–Receptor Protein Tyrosine Kinase," J.Med. Chem. 1994, vol. 37, pp. 1015–1027.

Maguire et al., "A New Series of PDGF Receptor Tyrosine Kinase Inhibitors: 3–Substituted Quinoline Derivatives," J.Med.Chem. 1994, vol. 37, pp. 2129–2137.

Dolle et al., "5,7–Dimethoxy–3–(4–pyridinyl)quinoline Is a Potent and Selective Inhibitor of Human Vascular β–Type Platelet–Derived Growth Factor Receptor Tyrosine Kinase," J.Med.Chem. 1994, vol. 37, pp. 2627–2629.

Bridges et al., "Enantioselective Inhibition of the Epidermal Growth Factor Receptor Tyrosine Kinase by 4–(α–Phenethylamino)quinazolines," Biorganic & Medicinal Chemistry, vol. 3, No. 12, pp. 1651–1656, 1995.

Ward et al., "Epidermal Growth Factor Receptor Tyrosine Kinase—Investigation of Catalytic Mechanism, Structure–Based Searching and Discovery of a Potent Inhibitor," Biochem.Pharmacology, vol. 48, No. 4, pp. 659–666 (1994).

Agrawal, "Studies on Potential Filaricides: Part XI" Chemical Abstracts, vol. 95, No. 1, 1981, Abstract No. 7199s, pp. 682–683; see abstract in Indian J. Chem. Sect. B, vol. 19B, No. 12, 1980, India, pp. 1084, 1087.

Connolly, et al., "Human Vascular Permeability Factor," J.Bio.Chem., vol. 264, No. 33, Nov. 1989, pp. 20017–20024.

Cullinan–Bove, et al., "Vascular Endothelial Growth Factor/ Vascular Permeability Factor Expression in the Rat Uterus . . . ," Endocrinology, vol. 133, No. 2, 1993, pp. 829–837.

Fan et al., "Controlling the Vasculature: Angiogenesis, Anti–Angiogenesis . . . ," TiPS Review, vol. 16, Feb. 1995, pp. 57–65.

Folkman, "Angiogenesis in Cancer, Vascular, Rheumatoid and Other Disease," Nature Medicine, vol. 1, No. 1, 1995, pp. 27–30.

Jakeman et al., "Developmental Expression of Binding Sites and Messenger Ribonucleic Acid . . . ," Endocrinology, vol. 133, No. 2, 1993, pp. 848–859.

Kim et al., "Inhibition of Vascular Endothelial Growth Factor–Induced Angiogenesis Suppresses Tumour Growth in Vivo," Nature, vol. 362, Apr. 1993, pp. 841–844.

Kolch et al., "Regulation of the Expression of the VEGF/ VPS and its Receptors: Role in Tumor Angiogenesis," Breast Cancer Research and Treatment, vol. 36, 1995, pp. 139–155.

Senger et al., "Vascular Permeability Factor (VPF, VEGF) in Tumor Biology, "Cancer and Metastasis Reveiw, vol. 12, 1993, pp. 303–324.

4-ANILINOQUINAZOLINE DERIVATIVES BEARING A HETEROARYL SUBSTITUTED AT THE 6-POSITION AND POSSESSING ANTI-CELL-PROLIFERATION PROPERTIES

This application is the national phase of international application PCT/GB95/02768, filed Nov. 28, 1995 which was designated the U.S.

The invention relates to quinazoline derivatives, or pharmaceutically-acceptable salts thereof, which possess anti-cell-proliferation activity such as anti-cancer activity and are accordingly useful in methods of treatment of the human or animal body. The invention also relates to processes for the manufacture of said quinazoline derivatives, to pharmaceutical compositions containing them and to their use in the manufacture of medicaments of use in the production of an anti-cell-proliferation effect in a warm-blooded animal such as man.

Many of the current treatment regimes for cell proliferation diseases such as psoriasis and cancer utilize compounds which inhibit DNA synthesis. Such compounds are toxic to cells generally but their toxic effect on rapidly dividing cells such as tumor cells can be beneficial. Alternative approaches to anti-proliferative agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumor cells (Bradshaw, *Mutagenesis*, 1986, 1, 91). Several such oncogenes give rise to the production of peptides which are receptors for growth factors. The growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al. *Ann. Reports in Med. Chem.* 1989, Chpt. 13).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43–73) based on families of growth factors which bind to different receptor tyrosine kinases. The classification includes Class I receptor tyrosine kinases comprising the EGF family of receptor tyrosine kinases such as the EGF, transforming growth factor at (TGFα), NEU, erbB, Xmrk, DER and let23 receptors, Class II receptor tyrosine kinases comprising the insulin family of receptor tyrosine kinases such as the insulin, IGFI and insulin-related receptor (IRR) receptors and Class III receptor tyrosine kinases comprising the platelet-derived growth factor (PDGF) family of receptor tyrosine kinases such as the PDGFα, PDGFβ and colony-stimulating factor 1 (CSF1) receptors. It is known that Class I kinases such as the EGF family of receptor tyrosine kinases are frequently present in common human cancers such as breast cancer (Sainsbury et al., *Brit. J. Cancer*, 1988, 58, 458; Guerin et al., *Oncogene Res.*, 1988, 3, 21), squamous cell cancer of the lung (Hendler et al., *Cancer Cells*, 1989, 7, 347), bladder cancer (Neal et al., *Lancet*, 1985, 366), oesophageal cancer (Mukaida et al., *Cancer*, 1991, 68, 142), gastrointestinal cancer such as colon, rectal or stomach cancer (Bolen et al., *Oncogene Res.*, 1987, 1, 149), leukaemia (Konaka et al., *Cell*, 1984, 37, 1035) and ovarian, bronchial or pancreatic cancer (European Patent Specification No. 0400586). As further human tumor tissues are tested for the EGF family of receptor tyrosine kinases it is expected that its widespread prevalance will be established in further cancers such as thyroid and uterine cancer. It is also known that-EGF type tyrosine kinase activity is rarely detected in normal cells whereas it is more frequently detectable in malignant cells (Hunter, *Cell*, 1987, 50, 823). It has been shown more recently (W J Gullick, *Brit. Med. Bull.*, 1991, 47, 87) that EGF receptors which possesses tyrosine kinase activity are overexpressed in many human cancers such as brain, lung squamous cell, bladder, gastric, colorectal, breast, head and neck, oesophageal, gynaecological and thyroid tumours.

Accordingly it has been recognised that an inhibitor of receptor tyrosine kinases should be of value as a selective inhibitor of the growth of mammalian cancer cells (Yaish et at. *Science*, 1988, 242, 933). Support for this view is provided by the demonstration that erbstatin, an EGF receptor tyrosine kinase inhibitor, specifically attenuates the growth in athymic nude mice of a transplanted human mammary carcinoma which expresses EGF receptor tyrosine kinase but is without effect on the growth of another carcinoma which does not express EGF receptor tyrosine kinase (Toi et al., *Eur. J. Cancer Clin. Oncol.*, 1990, 26, 722). Various derivatives of styrene are also stated to possess tyrosine kinase inhibitory properties (European Patent Application Nos. 0211363, 0304493 and 0322738) and to be of use as anti-tumor agents. The in vivo inhibitory effect of two such styrene derivatives which are EGF receptor tyrosine kinase inhibitors has been demonstrated against the growth of human squamous cell carcinoma inoculated into nude mice (Yoneda et al., *Cancer Research*, 1991, 51, 4430). Accordingly it has been indicated that Class I receptor tyrosine kinase inhibitors will prove to be useful in the treatment of a variety of human cancers. Various known tyrosine kinase inhibitors are disclosed in a more recent review by T R Burke Jr. (*Drugs of the Future*, 1992, 17, 119).

It is also expected that inhibitors of EGF type receptor tyrosine kinases will be useful in the treatment of other diseases of excessive cellular proliferation such as psoriasis (where TGFα is believed to be the most important growth factor) and benign prostatic hypertrophy (BPH).

It is known from European Patent Applications Nos. 0520722 and 0566226 that certain quinazoline derivatives which bear an anilino substituent at the 4-position possess receptor tyrosine kinase inhibitory activity. It is further known from European Patent Application No. 0602851 that certain quinazoline derivatives which bear a heteroarylamino substituent at the 4-position also possess receptor tyrosine kinase inhibitory activity.

It is further known from International Patent Application WO 92/20642 that certain aryl and heteroaryl compounds inhibit EGF and/or PDGF receptor tyrosine kinase. There is the disclosure of certain quinazoline derivatives therein but no mention is made of 4-anilinoquinazoline derivatives.

It is further known from European Patent Application No. 0635507 that certain tricyclic compounds which comprise a 5- or 6-membered ring fused to the benzo-ring of a quinazoline possess receptor tyrosine kinase inhibitory activity. It is also known from European Patent Application No. 0635498 that certain quinazoline derivatives which carry an amino group at the 6-position and a halogeno group at the 7-position possess receptor tyrosine kinase inhibitory activity.

The in vitro anti-proliferative effect of a 4-anilinoquinazoline derivative has been disclosed by Fry et al., *Science*, 1994, 265, 1093. It was stated that the compound 4-(3-bromoanilino)-6,7-dimethoxyquinazoline was a highly potent inhibitor of EGF receptor tyrosine kinase.

The in vivo inhibitory effect of a 4,5-dianilinophthalimide derivative which is an inhibitor of the EGF family of receptor tyrosine kinases has been demonstrated against the growth in BALB/c nude mice of a human epidermoid carcinoma A-431 or of a human ovarian carcinoma SKOV-3 (Buchdunger et al., *Proc. Nat. Acad. Sci.*, 1994, 91, 2334).

There is no disclosure in these documents of quinazoline derivatives which bear at the 4-position an anilino substituent and at the 6-position a heteroaryl substituent.

We have now found that certain novel 6-substituted-4-anilinoquinazoline derivatives possess anti-cell-proliferation properties which are believed to arise from their Class I receptor tyrosine kinase inhibitory activity.

According to the invention there is provided a quinazoline derivative of the formula I

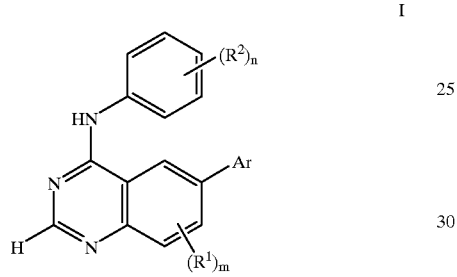

wherein m is 1 or 2;

each $R^1$ is independently hydrogen, halogeno, cyano, amino, nitro, carbamoyl, carboxy, (1–4C) alkoxycarbonyl, (1–4C)alkyl, (1–4C)alkylthio, (1–4C) alkylamino, di-[(1–4C)alkyl]amino, (2–4C) alkanoylamino or (1–4C)alkoxy;

n is 1, 2 or 3;

each $R^2$ is independently hydrogen, hydroxy, halogeno, trifluoromethyl, trifluoromethoxy, amino, nitro cyano, (1–4C)alkyl, (1–4C)alkoxy, (1–4C)alkylamino, di-[(1–4C)alkylamino, (1–4C)alkylthio, (1–4C) alkylsulphinyl, (1–4C)alkylsulphonyl, (2–4C ) alkanoylamino, (2–4C)alkanoyl or (1–3C) alkylenedioxy, or $R^2$ is a group of the formula —X—Q which is located para to the NH group in formula I and wherein X is a group of the formula CO, $C(R^3)_2$, $CH(OR^3)$, $C(R^3)_2$—$C(R^3)_2$, $C(R^3)$=$C(R^3)$, C≡C, $CH(CN)$, O, S, SO, $SO_2$, $CONR^3$, $SO_2NR^3$, $NR^3CO$, $NR^3SO_2$, $OC(R^3)_2$, $SC(R^3)_2$, $C(R^3)_2O$ or $C(R^3)_2S$ wherein each $R^3$ is independently hydrogen or (1–4C) alkyl, and Q is a phenyl or naphthyl group or a 5- or 6-membered heteroaryl moiety containing up to three heteroatoms selected from oxygen nitrogen and sulphur, which heteroaryl moiety is a single ring or is fused to a benzo ring, and wherein said phenyl or naphthyl group or heteroaryl moiety is optionally substituted with one, two or three substituents selected from halogeno, trifluoromethyl, cyano, carbamoyl, hydroxy, amino, nitro, (1–4C)alkyl, (1–4C)alkoxy, (1–4C )alkylamino, di-[(1–4C)alkyl]amino, (2–4(C) alkanoylamino, N-(1–4C)alkylcarbamoyl and N,N-di-[(1–4C)alkyl]carbamoyl; and Ar is a 5- or 9-membered nitrogen-linked heteroaryl moiety containing up to four nitrogen heteroatoms, or Ar is 2-oxo-4-imidazolin-1-yl, 2-oxo-1,2-dihydropyridin-1-yl, 4-oxo-1,4-dihydropyridin-1-yl, 2-oxo-1,2-dihydropyrimidin-1-yl, 4-oxo-3,4-dihydropyrimidin-3-yl, 2,4-dioxo-1,2,3,4-tetrahydropyrimidin-1-yl, 2-oxo-1,2-dihydropyrazin-1-yl, 2,3-dioxo-1,2,3,4-tetrahydropyrazin-1-yl, 3-oxo-2,3-dihydroypyridazin-2-yl or 3,6-dioxo-1,2,3,6-tetrahydropyridazin-1-yl or the corresponding thioxo analogues thereof, or 2-oxoindolin-1-yl, 2,3-dioxoindolin-1-yl, 2-oxo-2,3-dihydrobenzimidazol-1-yl, 3-oxo-2,3-dihydro-1H-indazol-1-yl, 3-oxo-2,3-dihydro-1H-indazol-2-yl, 2-oxo-1,2-dihydroquinolin-1-yl, 2-oxo-1,2,3,4-tetrahydroquinolin-1-yl, 1-oxo-1,2-dihydroisoquinolin-2-yl, 2-oxo-1,2-dihydroquinazolin-1-yl, 2,4-dioxo-1,2,3,4-tetrahydroquinazolin-1-yl, 2-oxo-1,2-dihydroquinoxalin-1-yl, 2,3-dioxo-1,2,3,4-tetrahydroquinoxalin-1-yl, 4-oxo-1,4-dihydrocinnolin-1-yl, 3,4-dioxo-1,2,3,4-tetrahydrocinnolin-1-yl or 3,4-dioxo-1,2,3,4-tetrahydrocinnolin-2-yl or the corresponding thioxo analogues thereof, and Ar is optionally substituted with one, two or three substituents selected from halogeno, hydroxy, amino, mercapto, carboxy, carbamoyl, (1–4C)alkyl, (1–4C) alkoxy, (1–4C)alkylamino, di-[(1–4C)alkyl]amino, (1–4C)alkylthio, (2–4C)alkanoyl, (1–4C) alkoxycarbonyl, (2–4C)alkanoylamino, N-(1–4C) alkylcarbamoyl, N,N-di-[(1–4C)alkyl]carbamoyl, N-[hydroxy-(2–4C)alkyl]carbamoyl, N,N-di-[hydroxy-(2–4C)alkyl]carbamoyl, N-[(1–4C)alkoxy-(2–4C)alkyl]carbamoyl, N,N-di-(1–4C)alkoxy-(2–4C) alkyl]carbamoyl, amino-(1–4C)alkyl, (1–4C) alkylamino-(1–4C)alkyl, di-[(1–4C)alkyl]amino-(1–4C)alkyl, pyrrolidin-1-yl-(1–4C)alkyl, piperidino-(1–4C)alkyl, morpholino-(1–4C)alkyl, piperazin-1-yl-(1–4(C)alkyl and 4-(1–4C)alkylpiperazin-1-yl-(1–4C) alkyl;

or a pharmaceutically-acceptable salt thereof.

According to a further aspect of the present invention there is provided a quinazoline derivative of the formula I wherein m is 1 or 2;

each $R^1$ is independently hydrogen, halogeno, cyano, amino, nitro, carbamoyl, carboxy, (1–4C) alkoxycarbonyl, (1–4C)alkyl, (1–4C)alkylthio, (1–4C) alkylamino, di-[(1–4C)alkyl]amino, (2–4C) alkanoylamino or (1–4C)alkoxy;

n is 1, 2 or 3;

each $R^2$ is independently hydrogen, hydroxy, halogeno, trifluoromethyl, trifluoromethoxy, amino, nitro, cyano, (1–4C)alkyl, (1–4C)alkoxy, (1–4C)alkylamino, di-[(1–4C)alkyl]amino, (1–4C)alkylthio, (1–4C) alkylsulphinyl, (1–4C)alkylsulphonyl, (2–4C) alkanoylamino, (2–4C)alkanoyl or (1–3C) alkylenedioxy; and Ar is a 5- or 9-membered nitrogen-linked heteroaryl moiety containing up to four nitrogen heteroatoms, or Ar is 2-oxo-1,2-dihydropyridin-1-yl, 4-oxo-1,4-dihyrolpyridin-1-yl, 2-oxo-1,2-dihydropyrimidin-1-yl, 4-oxo-3,4-dihydropyrimidin-3-yl, 2,4-dioxo-1,2,3,4-tetrahydropyrimidin-1-yl, 2-oxo-1,2-dihydropyrazin-1-yl, 2,3-dioxo-1,2,3,4-tetrahydrolpyrazin-1-yl, 3-oxo-2,3-dihyropyrdazin-2-yl or 3,6-dioxo-1,2,3,6-tetrahydropyridazin-1-yl or the corresponding thioxo anologues thereof, or 2-oxoindolin-1-yl, 2,3-dioxoindolin-1-yl, 2-oxo-2,3-dihyrobenzimidazol-1-yl, 3-oxo-2,3-dihydro-1H-indazol-1-yl, 3-oxo-2,3-dihydro-1H-indazol-2-yl, 2-oxo-1,2-dihydroquinolin- 1-yl, 2-oxo-1,2,3,4-tetrahydroquinolin-1-yl, 1-oxo-1,2-dihydroisoquinolin-2-yl, 2-oxo-1,2-dihydroquinazolin-1-yl, 2,4-dioxo-1,2,3,4-tetrahydroquinazolin-1-yl, 2-oxo-1,2-dihydroquinoxalin-1-yl, 2,3-dioxo-1,2,3,4-tetrahydroquinoxalin-1-yl, 4-oxo-1,4-dihydrocinnolin-1-yl, 3,4-dioxo-1,2,3,4-tetrahydrocinnolin-1-yl or 3,4-dioxo-1,2,3,4-tetrahydrocinnolin-2-yl or the corresponding thioxo analogues thereof, and Ar may optionally bear up to three substituents selected from halogeno, hydroxy, amino, mercapto, carboxy, carbamoyl, (1–4C)alkyl, (1–4C)alkoxy, (1–4C)alkylamino, di-[(1–4C)alkyl]amino, (1–4C)alkylthio, (2–4C)alkanoyl, (1–4C)alkoxycarbonyl, N-(1–4C)alkycarbamoyl, N,N-di-[(1–4C)alkyl]carbamoyl, N-[hydroxy-(1–4C)alkyl]carbamoyl, N,N-di-[hydroxy-(1–4C)alkyl]carbamoyl, N-[(1–4C)alkoxy-(1–4C)alkyl]carbamoyl and N,N-di-[(1–4C)alkoxy-(1–4C)alkyl]carbamoyl;

or a pharmaceutically-acceptable salt thereof.

In this specification the term "alkyl" includes both straight and branched chain alkyl groups but references to individual alkyl groups such as "propyl" are specific for the straight chain version only. An analogous convention applies to other generic terms.

The quinazolines of the formula I are unsubstituted at the 2-position. This is specifically indicated in formula I by the hydrogen atom at the 2-position. It is to be understood that the $R^1$ groups are located only on the benzo portion of the quinazoline ring.

It is also to be understood that, insofar as certain of the compounds of formula I defined above may exhibit the phenomenon of tautomerism, the invention encompasses any tautomeric form which possesses receptor tyrosine kinase inhibitory activity.

It is also to be understood that certain quinazoline derivatives of the formula I can exist in solvated as well as unsolvated forms such as, for example, hydrated forms. It is to he understood that the invention encompasses all such solvated forms which possess receptor tyrosinie kinase inhibitory activity.

Suitable values for the generic radicals referred to above include those set out below.

A suitable value for $R^1$ or $R^2$ when it is halogeno is, for example, fluoro, chloro, bromo or iodo; when it is (1–4C)alkoxycarbonyl is, for example, methoxycarbonyl, ethoxycarbonyl, propoxycarbonyl or butoxycarbonyl; when it is (1–4C)alkyl is, for example, methyl, ethyl, propyl, isopropyl, butyl, isobutyl, sec-butyl or tert-butyl; when it is (1–4C)alkylthio is, for example, methylthio, ethylthio or propylthio, when it is (1–4C)alkyl is, for example, methylamino, ethylamino or propylamino, when it is di-[(1–4C)alkyl]amino is, for example, dimethylamino, N-ethyl-N-methylamino, diethylamino, N-methyl-N-propylamino or diproylamino; when it is (2–4C)alkanoylamino is, for example, acetamido, propionamido or butyramido; and when it is (1–4C)alkoxy is, for example, methoxy, ethoxy, propoxy, isopropoxy or butoxy.

A suitable value for $R^2$ when it is (1–4C)alkylsulphinyl is, for example, methylsulphinyl, ethylsulphinyl or propylsulphinyl; when it is (1–4C)alkylsulphonyl is, for example, methylsulphonyl, ethylsulphonyl or propylsulphonyl; when it is (2–4C)alkanoyl is, for example, acetyl, propionyl or butyryl, and when it is (1–3C)alkylenedioxy is, for example, methylenedioxy, ethylenedioxy or propylenedioxy.

When $R^2$ is (1–3C)alkylenedioxy the oxygen atoms of each such group occupy adjacent positions on the anilino ring.

A suitable value for the $R^3$ group which may be present within X when said $R^3$ group is (1–4C)alkyl is, for example, methyl, ethyl or propyl.

A suitable value for Q when it is a naphthyl group is, for example, 1-naphthyl or 2-naphthyl.

A suitable value for Q when it is a 5- or 6-membered heteroaryl moiety containing up to three heteroatoms selected from oxygen, nitrogen and sulphur, which is a single ring is, for example, furyl, pyrrolyl, thienyl, pyridyl, oxazolyl, isoxazolyl, pyrazolyl, imidazolyl, thiazolyl, isothiazolyl, pyrazinyl, pyrimidinyl, pyridazinyl, 1,2,3-triazolyl, 1,2,4-triazolyl, oxadiazolyl, furazanyl or thiadiazolyl, or which is fused to a benzo ring is, for example, benzofuryl, indolyl, benzothienyl, quinolyl, isoquinolyl, benzoxazolyl, indazolyl, benzimidazolyl, benzothiazolyl, cinnolinyl, quinazolinyl, quinoxalinyl or benzotriazolyl. Said heteroaryl moiety may be attached to X through any available position. The optional substituents on Q may be located at any available position including on any available nitrogen heteroatom.

A suitable value for Ar when it is a 5- or 9-membered nitrogen-linked heteroaryl moiety containing up to four nitrogen heteroatoms is, for example, a fully-unsaturated monocyclic heteroaryl moiety such as 1-pyrrolyl, 1-pyrazolyl, 1-imidazolyl, 1,2,3-triazol-1-yl, 1,2,3-triazol-2-yl, 1,2,4-triazol-1-yl, 1,2,4-triazol-4-yl, 1H-tetrazol-1-yl and 2H-tetrazol-2-yl, or, for example, a fully-unsaturated bicyclic benzo-fused heteroaryl moiety such as 1-indolyl, 2-isoindolyl, 1H-indazol-1-yl, 2H-indazol-2-yl, benzimidazol-1-yl and benzo-1,2,3-triazol-1-yl.

Suitable values for the substituents which may be borne by Q or Ar include, for example:

| | |
|---|---|
| for halogeno: | fluoro, chloro, bromo and iodo; |
| for (1–4C)alkyl: | methyl, ethyl, propyl, isopropyl, butyl, and tert-butyl; |
| for (1–4C)alkoxy: | methoxy, ethoxy, propoxy, isopropoxy and butoxy; |
| for (1–4C)alkylamino: | methylamino, ethylamino and propylamino; |
| for di-[(1–4C)alkyl]-amino: | dimethylamino, N-ethyl-N-methylamino, diethylamino, N-methyl-N-propylamino and dipropylamino; |
| for (1–4C)alkylthio: | methylthio, ethylthio and propylthio; |
| for (2–4C)alkanoyl: | acetyl, propionyl and butyryl; |
| for (1–4C)alkoxy-carbonyl: | methoxycarbonyl, ethoxycarbonyl, propoxycarbonyl and butoxycarbonyl; |
| for (2–4C)alkanoyl-amino: | acetamido, propionamido and butyramido; |
| for N-(1–4C)alkyl-carbamoyl: | N-methylcarbamoyl, N-ethylcarbamoyl, N-propylcarbamoyl and N-butylcarbamoyl; |
| for N,N-di-[(1–4C)-alkyl]carbamoyl: | N,N-dimethylcarbamoyl, N,N-diethylcarbamoyl, N-ethyl-N-methylcarbamoyl, N,N-dipropylcarbamoyl and N,N-dibutylcarbamoyl; |
| for N-[hydroxy-(2–4C)-alkyl]carbamoyl: | N-[2-hydroxyethyl]carbamoyl, N-[3-hydroxypropyl]carbamoyl and N-[4-hydroxybutyl]carbamoyl; |
| for N,N-di-[hydroxy-(2–4C)alkyl]carbamoyl: | N,N-di-[2-hydroxyethyl]carbamoyl, N,N-di-[3-hydroxypropyl]carbamoyl and N,N-di-[4-hydroxybutyl]carbamoyl; |
| for N-[(1–4C)alkoxy-(2–4C)alkyl]carbamoyl: | N-[2-methoxyethyl]carbamoyl, N-[2-ethoxyethyl]carbamoyl, N-[3-methoxypropyl]carbamoyl and N-[4-methoxybutyl]carbamoyl; |
| for N,N-di-[(1–4C)-alkoxy-(2–4C)alkyl]-carbamoyl: | N,N-di-[2-methoxyethyl]carbamoyl, N,N-di-[2-ethoxyethyl]carbamoyl, N,N-di-[3-methoxypropyl]carbamoyl and N,N-di-[4-methoxybutyl]carbamoyl; |
| for amino-(1–4C)alkyl: | aminomethyl, 2-aminoethyl, 3-aminopropyl and 4-aminobutyl; |
| for (1–4C)alkylamino-(1–4C)alkyl: | methylaminomethyl, ethylaminomethyl, 2-methylaminoethyl, 2-ethylaminoethyl and 3-methylaminopropyl; |

-continued

| | |
|---|---|
| for di-[(1–4C)alkyl]-amino-(1–4C)alkyl: | dimethylaminomethyl, diethylaminomethyl, 2-dimethylaminoethyl, 2-(N-ethyl-N-methylamino)ethyl, 2-diethylaminoethyl and 3-dimethylaminopropyl; |
| for pyrrolidin-1-yl-(1–4C)alkyl: | pyrrolidin-1-ylmethyl, 2-(pyrrolidin-1-yl)ethyl and 3-(pyrrolidin-1-yl)propyl; |
| for piperidino-(1–4C)-alkyl: | piperidinomethyl, 2-piperidinomethyl and 3-piperidinopropyl; |
| for morpholino-(1–4C)-alkyl: | morpholinomethyl, 2-morpholinoethyl and 3-morpholinopropyl; |
| for piperazin-1-yl-(1–4C)alkyl: | piperazin-1-ylmethyl, 2-piperazin-1-ylethyl and 3-piperazin-1-ylpropyl; |
| for 4-(1–4C)alkylpiper-azin-1-yl-(1–4C)alkyl: | 4-methylpiperazin-1-ylmethyl, 2-(4-methylpiperazin-1-yl)ethyl and 3-(4-methylpiperazin-1-yl)propyl. |

A suitable pharmaceutically-acceptable salt of a quinazoline derivative of the invention is, for example, an acid-addition salt of a quinazoline derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a quilazolinie derivative of the invention which is sufficiently acidic is an alkali metal salt, for example a sodium or potassium salt, an alkaline earth metal salt, for example a calcium of magnesium salt, an ammonium salt or a salt with an organic base which affords a physiologically-acceptable cation, for example a salt with methylamine, dimethylamine, trimethylamine, piperidine, miorpholine or tris-(2-hydroxyethyl)amine.

Particular novel coin pounds of the invention include, for example, quinazoline derivatives of the formula I, or pharmaceutically-acceptable salts thereof, wherein:

(a) m is 1 and $R^2$ is selected from hydrogen, halogeno and (1–4C)alkoxy; and Ar, n and $R^2$ have any of the meanings defined hereinbefore or in this section relating to particular novel compounds of the invention, (b) n is 1 or 2 and each $R^2$ is independently hydrogen, halogeno, trifluoromethyl, trifluoromethoxy, nitro, cyano, (1–4C)alkyl or (1–4C)alkoxy; and Ar, m and $R^1$ have any of the meanings defined hereinbefore or in this section relating to particular novel compounds of the invention;

(c) n is 1 or 2, one $R^2$ is a group of the formula —X—Q which is located para to the NH group in formula I and wherein X is a group of the formula CO, $C(R^3)_2$, $CH(OR^3)$, $OC(R^3)_2$ or $SC(R^3)_2$, wherein each $R^3$ is independently hydrogen or (1–4C)alkyl, and Q is phenyl, furyl, pyrrolyl, thienyl, pyridyl, oxazolyl, imidazolyl, thiazolyl, pyrimidinyl, 1,2,4-triazolyl, oxadiazolyl or thiadiazolyl which is optionally substituted with one or two substituents selected from halogeno, cyano, (1–4C)alkyl and (1–4C)alkoxy, and the other $R^2$ (if present) is selected from halogeno, trifluoromethyl, cyano and (1–4C)alkyl; and Ar, m and $R^1$ have any of the meanings defined hereinbefore or in this section relating to particular novel compounds of the invention;

(d) n is 1 or 2, one $R^2$ is a group of the formula —X—Q which is located para to the NH group in formula I and wherein X is a group of the formula CO or $OCH_2$, and Q is phenyl, furyl, thienyl, pyridyl, oxazolyl, imidazolyl or thiazolyl which is optionally substituted with a substituent selected from halogen and (1–4C)alkyl, and the other $R^2$ (if present) is selected from halogen and (1–4C)alkyl; and Ar, m and $R^1$ have any of the meanings defined hereinbefore or in this section relating to particular novel compounds of the invention;

(e) Ar is a 5- or 9-membered nitrogen-linked heteroaryl moiety containing up to four nitrogen heteroatoms which is optionally substituted with one, two or three substituents as defined hereinbefore for Ar; and m, n, $R^1$ and $R^2$ have any of the meanings defined hereinbefore or in this section relating to particular novel compounds of the invention;

(f) Ar is 2-oxo-1,2-dihydropyridin-1-yl, 4-oxo-1,4-dihydropyridin-1-yl, 2-oxo-1,2-dihydropyrimidin-1-yl, 4-oxo-3,4-dihydropyrimidin-3-yl, 2,4-dioxo-1,2,3,4-tetrahydropyrimidin-1-yl, 2-oxo-1,2-dihydrropyrazin-1-yl, 2,3-dioxo-1,2,3,4-tetrahydropyrazin-1-yl, 3-oxo-2,3-dihydrpyridazin-2-yl or 3,6-dioxo-1,2,3,6-tetrahydropyridazin-1-yl or the corresponding thioxo analogues thereof, or 2-oxoindolin-1-yl, 2,3-dioxoindolin-1-yl, 2-oxo-2,3-dihydrobenzimidazol-1-yl, 3-oxo-2,3-dihydro-1-indazol-1-yl, 3-oxo-2,3-dihydro-1H-indazol-2-yl, 2-oxo-1,2-dihydroquinolin-1-yl, 2-oxo-1,2,3,4-tetrahydroquinolin-1-yl, 1-oxo-1,2-dihydroisoquinolin-2-yl, 2-oxo-1,2-dihydroquinolin-1-yl, 2,4-dioxo-1,2,3,4-tetrahydroquinazolin-1-yl, 2-oxo-1,2-dihydroquinoxalin-1-yl, 2,3-dioxo-1,2,3,4-tetrahydroquinazolin-1-yl, 4-oxo-1,4-dihydrocinnolin-1-yl, 3 4-dioxo-1,2,3,4-tetrahydrocinnolin-1-yl or 3,4-(dioxo-1,2,3,4-tetrahydrocinnolin-2-yl or the corresponding thioxo analogues therefor, and Ar is optionally substituted with one, two or three substituents as defined hereinbefore for Ar; and m, n, $R^1$ and $R^2$ have any of the meanings defined hereinbefore or in this section relating to particular novel compounds of the invention;

(g) Ar is a 5-membered nitrogen-linked fully-unsaturated monocyclic heteroaryl moiety containing up to four nitrogen heteroatoms which is optionally substituted with one or two substituents selected from those defined hereinbefore for Ar; and m, n, $R^1$ and $R^2$ have any of the meanings defined hereinbefore or in this section relating to particular novel compounds of the invention;

(h) Ar is a 9-membered nitrogen-linked fully-unsaturated bicyclic benzo-fused heteroaryl moiety containing up to three nitrogen heteroatoms which is optionally substituted with one or two substituents selected from those defined hereinbefore for Ar; and in n, $R^1$ and $R^2$ have any of the meanings defined hereinbefore or in this section relating to particular novel compounds of the invention;

(i) Ar is 2-oxo-1,2-dihydropyridin-1-yl, 4-oxo-1,4-dihydropyridin-1-yl, 2-oxo-1,2-dihydropyrimidin-1-yl, 4-oxo-3,4-dihydropyrimidin-3-yl, 2,4-dioxo-1,2,3,4-tetrahydropyrimidin-1-yl, 2-oxo-1,2-dihydropyrazin-1-yl, 2,3-dioxo-1,2,3,4-tetrahydropyrazin-1-yl, 3-oxo-2,3-dihydropyridazin-2-yl or 3,6-dioxo-1,2,3,6-tetrahydropyridazin-1-yl, and Ar is optionally substituted with one or two further substituents selected from those defined hereinbefore for Ar, and m, n, $R^1$ and $R^2$ have any of the meanings defined hereinbefore or in this section relating to particular novel compounds of the invention; or (j) Ar is 2-oxoindolin-1-yl, 2,3-dioxoindolin-1-yl, 2-oxo-2,3-dihydrobenzimdazol-1-yl, 3-oxo-2,3-dihydro-1H-indazol-1-yl, 3-oxo-2,3-dihydro-1H-inidazol-2-yl, 2-oxo-1,2-dihydroquinolin-1-yl, 2-oxo-1,2,3,4-tetrahydroquinolin-1-yl, 1-oxo-1,2-dihydroisoquinolin-2-yl, 2-oxo-1,2-dihydroquinazolin-1-yl, 2,4-dioxo-1,2,3,4-tetrahydroquinazolin-1-yl, 2-oxo-1 2-dihydroquinoxalin-1-yl, 2,3-dioxo-1,2,3,4-tetrahydroquinoxalin-1-yl, 4-oxo-1,4-dihydrocinniolin-1-yl, 3,4-dioxo-1,2,3,4-tetrahydrocinnolin-1-yl or 3,4-dioxo1,2,3,4-tetrahydrocinnolin-2-yl, and Ar is optionally substituted with one or two further substituents selected from those defined hereinbefore for Ar; and m, n, $R^1$ and $R^2$ have any of the meanings defined hereinbefore or in this section relating to particular novel compounds of the invention.

A preferred compound of the invention is a quinazoline derivative of the formula I wherein m is 1 and $R^1$ is selected from hydrogen, fluoro, chloro, bromo, methoxy and ethoxy, n is 1 or 2 and each $R^2$ is independently hydrogen, hydroxy, fluoro, chloro, bromo, trifluoromethyl, trifluoromethoxy, amino, nitro, cyano, methyl, ethyl, methoxy, ethoxy, methylamino, ethylamino, dimethylamino, diethylamino, methylthio, ethylthio, propylthio, methylsulphinyl, ethylsulphinyl, propylsulphinyl, methylsulphonyl, ethylsulphonyl, propylsulphonyl, acetamido, propionamido, butyramido, acetyl, propionyl, butyryl, methylenedioxy, ethylenedioxy or propylenedioxy;

Ar is 1-pyrrolyl, 1-pyrazolyl, 1-imidazolyl, 1,2,3-triazol-1-yl, 1,2,3-triazol-2-yl, 1,2,4-triazol-1-yl, 1,2,4-triazol-4-yl, 1H-tetrazol-1-yl and 2H-tetrazol-2-yl, 1-indolyl, 2-isoindolyl, 1H-indazol-1-yl, 2H-indazol-2-yl, 1-benzimidazolyl or benzo-1,2,3-triazol-1-yl, and Ar may bear one or two substituents independently selected from fluoro, chloro, bromo, methyl, ethyl, methoxy, ethoxy, methylamino, ethylamino, dimethylamino, diethylamino, methylthio, ethylthio, acetyl, methoxycarbonyl, ethoxycarbonyl, N-methylcarbamoyl, N-ethylcarbamoyl, N,N-dimethylcarbamoyl, N,N-diethylcarbamoyl, N-[2-hydroxyethyl]carbamoyl, N-[3-hydroxypropyl]carbamoyl, N,N-di-[2-hydroxyethyl]carbamoyl, N,N-di-[3-hydroxypropyl]carbamoyl, N-[2-methoxyethyl]carbamoyl and N,N-di-[2-methoxyethyl]carbamoyl;

or a pharmaceutically-acceptable salt thereof;

A further preferred compound of the invention is a quinazoline derivative of the formula I wherein m is 1 and $R^1$ is selected from hydrogen, fluoro, chloro, bromo, methoxy and ethoxy, n is 1 or 2 and each $R^2$ is independently hydrogen, hydroxy, fluoro, chloro, bromo, trifluoromethyl, trifluoromethoxy, amino, nitro, cyano, methyl, ethyl, methoxy, ethoxy, methylamino, ethylamino, dimethylamino, diethylamino, methylthio, ethylthio, propylthio, methylsulphinyl, ethylsulphinyl, propylsulphinyl, methylsulphonyl, ethylsulphonyl, propylsulphonyl, acetamido, propionamido, butyramido, acetyl, propionyl, butyryl, methylenedioxy, ethylenedioxy or propylenedioxy;

Ar is 2-oxo-1,2-dihydropyridin-1-yl, 4-oxo-1,4-dihydropyridin-1-yl, 2-oxo-1,2-dihydropyrimidin-1-yl, 4-oxo-3,4-dihydropyrimidin-3-yl, 2,4-dioxo-1,2,3,4-tetrahydropyrimidin-1-yl, 2-oxo-1,2-dihydropyrazin-1-yl, 2,3-dioxo-1,2,3,4-tetrahydropyrazin-1-yl, 3-oxo-2,3-dihydropyridazin-2-yl and 3,6-dioxo-1,2,3,6-tetrahydropyridazin-1-yl, or the corresponding thioxo analogues thereof such as 2-thioxo-1,2-dihydropyridin-1-yl, 2-oxoindolin-1-yl, 2,3-dioxoindolin-1-yl, 2-oxo-2,3-dihydrobenzimidazol-1-yl, 3-oxo-2,3-dihydro-1H-indazol-1-yl, 3-oxo-2,3-dihydro-1H-indazol-2-yl, 2-oxo-1,2-dihydroquinolin-1-yl, 2-oxo-1,2,3,4-tetrahydroquinolin-1-yl, 1-oxo-1,2-dihydroisoquinolin-2-yl, 2-oxo-1,2-dihydroquinazolin-1-yl, 2,4-dioxo-1,2,3,4-tetrahydroquinazolin-1-yl, 2-oxo-1,2-dihydroquinoxalin-1-yl, 2,3-dioxo-1,2,3,4-tetrahydroquinoxalin-1-yl, 4-oxo-1,4-dihydrocinnolin-1-yl, 3,4-dioxo-1,2,3,4-tetrahydrocinnolin-1-yl and 3,4-dioxo-1,2,3,4-tetrahydrocinnolin-2-yl or the corresponding thioxo analogues thereof such as 2-thioxoindolin-1-yl, and Ar may bear one or two substituents independently selected from fluoro, chloro, bromo, methyl, ethyl, methoxy, ethoxy, methylamino, ethylamino, dimethylamino, diethylamino, methylthio, ethylthio, acetyl, methoxycarbonyl, ethoxycarbonyl, N-methylcarbamoyl, N-ethylcarbamoyl, N,N-dimethylcarbamoyl, N,N-diethylcarbamoyl, N-[2-hydroxyethyl]carbamoyl, N-[3-hydroxypropyl]carbamoyl, N,N-di-[2-hydroxyethyl]carbamoyl, N,N-di-[3-hydroxypropyl]carbamoyl, N-[2-methoxyethyl]carbamoyl and N,N-di-[2-methoxyethyl]carbamoyl;

or a pharmaceutically-acceptable salt thereof;

A further preferred compound of the invention is a quinazoline derivative of the formula I wherein m is 1 and $R^1$ is hydrogen, 7-fluoro, 7-chloro or 7-methoxy;

n is 1or 2 and each $R^2$ is independently fluoro, chloro or methyl; and

Ar is 1-pyrrolyl, 1-pyrazolyl, 1-imidazolyl, 1,2,3-triazol-1-yl, 1,2,4-triazol-1-yl, 1,2,4-triazol-4-yl, 1-indolyl, 1H-indazol-1-yl, 1-benzimidazolyl or 1,2,3-triazol-1-yl which optionally bears one or two substituents selected from fluoro, chloro, bromo, methyl and ethyl;

or a pharmaceutically-acceptable salt thereof.

A further preferred compound of the invention is a quinazoline derivative of the formula I wherein m is 1 and $R^1$ is hydrogen, 7-fluoro, 7-chloro or 7-methoxy;

n is 1 or 2 and each $R^2$ is independently fluoro, chloro or methyl; and

Ar is 2-oxo-1,2-dihydropyridin-1-yl, 2-oxo-1,2-dihydropyrimidin-1-yl, 2,4-dioxo-1,2,3,4-tetrahydropyrimidin-1-yl, 2,3-dioxo-1,2,3,4-tetrahydropyrazin-1-yl, 2-oxoindolin-1-yl, 2,3-dioxoindolin-1-yl, 2-oxo-2,3-dihydrobenzimidazol-1-yl, 2-oxo-1,2-dihydroquinolin-1-yl, 2-oxo-1,2,3,4-tetrahydroquinolin-1-yl, 2,4-dioxo-1,2,3,4-tetrahydroquinazolin-1-yl or 2,3-dioxo-1,2,3,4-tetrahydroquinoxalin-1-yl which optionally bears one or two substituents selected from fluoro, chloro, bromo, methyl and ethyl; or a pharmaceutically-acceptable salt thereof.

A further preferred compound of the invention is a quinazoline derivative of the formula I wherein $(R^1)_m$ is hydrogen;

$(R^2)_n$ is 3-chloro-4-fluoro, 3,4-dichloro, 3,4-difluoro, 3-chloro, 3-fluoro or 3-methyl; and Ar is 1-pyrazolyl, 1-imidazolyl, 1,2,4-triazol-1-yl, 1,2,4-triazol4-yl or 1-benzimidazolyl;

or a pharmaceutically-acceptable acid-addition salt thereof.

A further preferred compound of the invention is a quinazoline derivative of the formula I wherein $(R^1)_m$ is hydrogen;

$(R^2)_n$ is 3-chloro-4-fluoro, 3,4-dichloro, 3,4-difluoro, 3-chloro, 3-fluoro or 3-methyl; and Ar is 2-oxo-1,2-dihydropyridin-1-yl, 2-oxoindolin-1-yl, 2-oxo-2,3-dihydrobenzimidazol-1-yl, 2-oxo-1,2-dihydroquinolin-1-yl or 2-oxo-1,2,3,4-tetrahydroquinolin-1-yl;

or a pharmaceutically-acceptable acid-addition salt thereof.

A further preferred compound of the invention is a quinazoline derivative of the formula I wherein $(R^1)_m$ is hydrogen;

$(R^2)_n$ is 3-chloro-4-fluoro, 3,4-dichloro or 3-methyl; and

Ar is 1-imidazolyl, 1-benzimidazolyl or 2-oxo-1,2-dihydropyridin-1-yl;
or a pharmaceutically-acceptable acid-addition salt thereof.

A specific preferred compound of the invention is the following quinazoline derivative of the formula I:

4-(3-methylanilino)-6-(1-imidazolyl)quinazoline or 4-(3-chloro-4-fluoroanilino)-6-(1-imidazolyl)quinazoline, or a pharmaceutically-acceptable salt thereof.

A further preferred compound of the invention is a quinazoline derivative of the formula I wherein m is 1 and $R^1$ is hydrogen, 7-fluoro, 7-chloro or 7-methoxy;

n is 1 or 2 and each $R^2$ is independently fluoro, chloro, bromo, methyl and ethyl, or one $R^2$ is a group of the formula —X—Q which is located para to the NH group in formula I and wherein X is a group of formula CO or $OCH_2$ and Q is phenyl or 2-pyridyl, and the other $R^2$ (if present) is selected from fluoro, chloro, bromo, methyl and ethyl; and Ar is 1-pyrazoyl, 1-imidazolyl, 1,2,4-triazol-1-yl or 1-benzimidazolyl which optionally bears a substituent selected from fluoro, chloro, bromo, methyl and ethyl;
or a pharmaceutically-acceptable salt thereof.

A further preferred compound of the invention is a quinazoline derivative of the formula I wherein m is 1 and $R^1$ is hydrogen, 7-fluoro, 7-chloro or 7-methoxy;

n is 1 or 2 and each $R_2$ independently fluoro, chloro, bromo, methyl and ethyl, or one $R^2$ is a group of the formula —X—Q which is located para to the NH group in formula I and wherein X is a group of formula CO or $OCH_2$, and Q is phenyl or 2-pyridyl, and the other $R^2$ (if present) is selected from fluoro, chloro, bromo, methyl and ethyl; and Ar is 2-oxo-1,2-dihydropyridin-1-yl;
or a pharmaceutically-acceptable acid-addition salt thereof.

A further preferred compound of the invention is a quinazoline derivative of the formula I wherein $(R^1)_m$ is hydrogen or 7-methoxy;

$(R^2)_n$ is 3-chloro-4-fluoro, 3,4-dichloro, 2,4-difluoro, 3,4-difluoro, 3-methyl, 2-fluoro-4-(2-pyridylmethoxy), 3-methyl-4-(2-pyridylmethoxy) or 4-benzoyl-3-chloro;
and Ar is 1-imidazolyl, 1-benzimidazolyl, 1-pyrazolyl, 1,2,4-triazol-1-yl or 2-oxo-1,2-dihydropyridin-1-yl;
or a pharmaceutically-acceptable acid-addition salt thereof.

A further specific preferred compound of the invention is the following quinazoline derivative of the formula I:

6-(1-imidazolyl)-4-[3-methyl4-(2-pyridylmethoxy)anilino]quinazoline or 4-(4-benzoyl-3-chloroanilino)-6-(1-imidazolyl)quinazoline;
or a pharmaceutically-acceptable acid-addition salt thereof.

A quinazoline derivative of the formula I, or a pharmaceutically-acceptable salt thereof, may be prepared by any process known to be applicable to the preparation of chemically-related compounds. Suitable processes include, for example, those illustrated in European Patent Applications Nos. 0520722, 0566226, 0602851, 0635507 and 0635498.

Such processes, when used to prepare a quinazoline derivative of the formula I, or a pharmaceutically-acceptable salt thereof, are provided as a further feature of the invention and are illustrated by the following representative examples in which, unless otherwise stated, Ar, $R^1$, m, n and $R^2$ have any of the meanings defined hereinbefore for a quinazoline derivative of the formula I. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

(a) The reaction, conveniently in the presence of a suitable base, of a quinazoline of the formula II

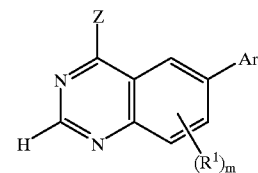

wherein Z is a displaceable group, with an aniline of the formula III

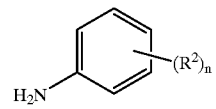

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride.

A suitable displaceable group Z is, for example, a halogeno, alkoxy, aryloxy or sulphonyloxy group, for example a chloro, bromo, methoxy, phenoxy, methanesulphonyloxy or toluene-p-sulphonyloxy group. The reaction is conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 250° C., preferably in the range 40 to 80° C.

The quinazoline derivative of the formula I may be obtained from this process in the form of the free base or alternatively it may be obtained in the form of a salt with the acid of the formula H-Z wherein Z has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

(b) The reaction, conveniently in the presence of a suitable base as defined hereinbefore, of a quinazoline of the formula IV

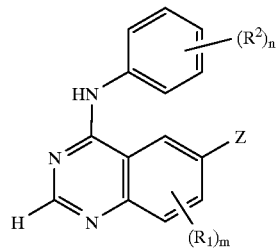

IV wherein Z is a displaceable group as defined hereinbefore, with a group of the formula Ar—H where Ar is as defined hereinbefore.

The reaction is conveniently carried out in the presence of a suitable inert solvent or diluent as defined hereinbefore, and at a temperature in the range, for example, 10 to 250° C., preferably in the range 100 to 200° C.

When a pharmaceutically-acceptable salt of a quinazoline derivative of the formula I is required, for example an acid-addition salt, it may be obtained, for example, by reaction of said compound with, for example, a suitable acid using a conventional procedure.

Many of the intermediates defined herein are novel, for example, those of the formula II and these are provided as a further feature of the invention.

As stated hereinbefore the quinazoline derivative defined in the present invention possesses anti-cell-proliferation activity such as anti-cancer activity which is believed to arise from the Class I receptor tyrosine kinase inhibitory activity of the compound. These properties may be assessed, for example, using one or more of the procedures set out below:

(a) An in vitro assay which determines the ability of a test compound to inhibit the enzyme EGF receptor tyrosine kinase. Receptor tyrosine kinase was obtained in partially purified form from A-431 cells (derived from human vulval carcinoma) by the procedures described below which are related to those described by Carpenter et al., *J. Biol. Chem.*, 1979, 254, 4884, Cohen et al, *J. Biol. Chem.*, 1982, 257, 1523 and by Braun et al., *J. Biol. Chem.*, 1984, 259, 2051.

A-431 cells were grown to confluence using Dulbecco's modified Eagle's medium (DMEM) containing 5% fetal calf serum (FCS). The obtained cells were homogenised in a hypotonic borate/EDTA buffer at pH 10.1. The homogenate was centrifuged at 400 g for 10 minutes at 0–4° C. The supernatant was centrifuged at 25,000 g for 30 minutes at 0–4° C. The pelleted material was suspended in 30 mM Hepes buffer at pH 7.4 containing 5% glycerol, 4 mM benzamidine and 1% Triton X-100, stirred for 1 hour at 0–4° C., and recentrifuged at 100,000 g for 1 hour at 0–4° C. The supernatant, containing solubilised receptor tyrosine kinase, was stored in liquid nitrogen.

For test purposes 40 μl of the enzyme solution so obtained was added to a mixture of 400 μl of a mixture of 150 mM Hepes buffer at pH 7.4, 500 μM sodium orthovanadate, 0.1% Triton X-100, 10% glycerol, 200 μl water, 80 μl of 25 mM DTT and 80 μl of a mixture of 12.5 mM manganese chloride, 125 mM magnesium chloride and distilled water. There was thus obtained the test enzyme solution.

Each test compound was dissolved in dimethylsulphoxide (DMSO) to give a 50 mM solution which was diluted with 40 mM Hepes buffer containing 0.1% Triton X-100, 10% glycerol and 10% DMSO to give a 500 μM solution. Equal volumes of this solution and a solution of epidermal growth factor (EGF; 20 μg/ml) were mixed.

[γ-$^{32}$P]ATP (3000 Ci/mM, 250 μCi) was diluted to a volume of 2 ml by the addition of a solution of ATP (100 μM) in distilled water. An equal volume of a 4 mg/ml solution of the peptide Arg-Arg-Leu-Ile-Glu-Asp-Ala-Glu-Tyr-Ala-Ala-Arg-Gly in a mixture of 40 mM Hepes buffer at pH 7.4, 0.1% Triton X-100 and 10% glycerol was added.

The test compound/EGF mixture solution (5 μl) was added to the test enzyme solution (10 μl) and the mixture was incubated at 0–4° C. for 30 minutes. The ATP/peptide mixture (10 μl) was added and the mixture was incubated at 25° C. for 10 minutes. The phosphorylation reaction was terminated by the addition of 5% trichloroacetic acid (40 μl) and bovine serum albumin (BSA; 1 mg/ml, 5 μl). The mixture was allowed to stand at 4° C. for 30 minutes and then centrifuged. An aliquot (40 μl) of the supernatant was placed onto a strip of Whatman p 81 phosphocellulose paper. The strip was washed in 75 mM phosphoric acid (4×10 ml) and blotted dry. Radioactivity present in the filter paper was measured using a liquid scintillation counter (Sequence A). The reaction sequence was repeated in the absence of the EGF (Sequence B) and again in the absence of the test compound (Sequence C).

Receptor tyrosine kinase inhibition was calculated as follows:

$$\% \text{ Inhibition} = \frac{100 - (A - B)}{C - B} \times 100$$

The extent of inhibition was then determined at a range of concentrations of test compound to give an IC$_{50}$ value.

(b) An in vitro assay which determines the ability of a test compound to inhibit the EGF-stimulated growth of the human naso-pharyngeal cancer cell line KB. KB cells were seeded into wells at a density of 1×10$^4$–1.5×10$^4$ cells per well and grown for 24 hours in DMEM supplemented with 5% FCS (charcoal-stripped). Cell growth was determined after incubation for 3 days by the extent of metabolism of MTT tetrazolium dye to furnish a bluish colour. Cell growth was then determined in the presence of EGF (10 ng/ml) or in the presence of EGF (10 ng/ml) and a test compound at a range of concentrations. An IC$_{50}$ value could then be calculated.

(c) An in vivo assay in a group of male rats which determines the ability of a test compound (usually administered orally as a ball-milled suspension in 0.5% polysorbate) to inhibit the stimulation of liver hepatocyte growth caused by the administration of the growth factor TGFα (400 μg/kg subcutaneously, usually dosed twice, 3 and 7 hours respectively after the administration of the test compound).

In a control group of rats, the administration of TGFα causes on average a 5-fold stimulation of liver hepatocyte growth.

Cell-growth in the control and test animals is determined as follows:

On the morning of the day after the dosing of the test compound (or 0.5% polysorbate in the control group), the animals are dosed with bromodeoxyuridine (BrdU; 100 mg/kg intraperitoneally). The animals are killed four hours later and the livers are excised. Slices are cut from each liver and the uptake of BrdU is determined by a conventional immunohistochemical technique similar to that described on pages 267 and 268 of an article by Goldsworthy et al. in Chemically Induced Cell Proliferation: Implications for Risk Assessment, Wiley-Liss Inc., 1991, pages 253–284. Further tests were carried out using a range of doses of the test compounds to allow the calculation of an approximate $ED_{50}$ value for the inhibition of liver hepatocyte proliferation as determined by inhibition of the uptake of BrdU.

(d) An in-vivo assay in a group of athymic nude mice (strain ONU:Alpk) which determines the ability of a test compound (usually administered orally as a ball-milled suspension in 0.5% polysorbate) to inhibit the growth of xenografts of the human vulval epidermoid carcinoma cell line A431.

A431 cells were maintained in culture in DMEM supplemented with 5% FCS and 2 mM glutamine. Freshly cultured cells were harvested by trypsinization and injected subcutaneously (10 million cells/0.1 ml/mouse) into both flanks of a number of donor nude mice. When sufficient tumour material was available (after approximately 9 to 14 days), fragments of tumour tissue were transplanted into the flanks of recipient nude mice (test day 0). On the eighth day after transplantation (test day 7) groups of 8 to 10 mice with similar-sized tumours were selected and dosing of the test compound was commenced. Once-daily dosing of test compound was continued for a total of 13 days (test days 7 to 19 inclusive). In some studies the dosing of the test compound was continued beyond test day 19, for example to test day 26. In each case, on the following day the animals were killed and final tumour volume was calculated from measurements of the length and width of the tumours. Results were calculated as a percentage inhibition of tumour volume relative to untreated controls.

Although the pharmacological properties of the compounds of the formula I vary with structural change as expected, in general activity possessed by compounds of the formula I may be demonstrated at the following concentrations or doses in one or more of the above tests (a), (b), (c) and (d):

| | |
|---|---|
| Test (a):- | $IC_{50}$ in the range, for example, 0.01–1 μM; |
| Test (b):- | $IC_{50}$ in the range, for example, 0.1–10 μM; |
| Test (c):- | $ED_{50}$ in the range, for example, 1–100 mg/kg; |
| Test (d):- | 20 to 70% inhibition of tumour volume from a daily dose in the range, for example, 50 to 400 mg/kg. |

Thus, by way of example, the compound 4-(3-methylanilino)-6-(1-imidazolyl)quinazoline has an $IC_{50}$ of 0.026 μM in Test (a), an $IC_{50}$ of 0.51 μM in Test (b), an $ED_{50}$ of <12.5 mg/kg in Test (c) and gives 63% inhibition in Test (d) at a dosage of 200 mg/kg/day.

According to a further aspect of the invention there is provided a pharmaceutical composition which comprises a quinazoline derivative of the formula I, or a pharmaceutically-acceptable salt thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The quinazoline derivative will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–100 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a quinazoline derivative of the formula I as defined hereinbefore for use in a method of treatment of the human or animal body by therapy.

We have now found that the compounds of the present invention possess anti-cell-proliferation properties which are believed to arise from their Class I receptor tyrosine kinase inhibitory activity. Accordingly the compounds of the present invention are expected to be useful in the treatment of diseases or medical conditions mediated alone or in part by Class I receptor tyrosine kinase enzymes, i.e. the compounds may be used to produce a Class I receptor tyrosine kinase inhibitory effect in a warm-blooded animal in need of such treatment. Thus the compounds of the present invention provide a method for treating the proliferation of malignant cells characterised by inhibition of Class I receptor tyrosine kinase enzymes, i.e. the compounds may be used to produce an anti-proliferative effect mediated alone or in part by the inhibition of Class I receptor tyrosine kinase. Accordingly the compounds of the present invention are expected to be useful in the treatment of cancer by providing an anti-proliferative effect, particularly in the treatment of Class I receptor tyrosine kinase sensitive cancers such as cancers of the breast, lung, colon, rectum, stomach, prostate, bladder, pancreas and ovary. The compounds of the present invention are also expected to be useful in the treatment of other cell-proliferation diseases such as psoriasis.

Thus according to this aspect of the invention there is provided the use of a quinazoline derivative of the formula I, or a pharmaceutically-acceptable salt thereof, as defined hereinbefore in the manufacture of a medicament for use in the production of an anti-cell-proliferation effect in a warm-blooded animal such as man.

According to a further feature of this aspect of the invention there is provided a method for producing an anti-cell-proliferation effect in a warm-blooded animal, such as man, in need of such treatment which comprises administering to said animal an effective amount of a quinazoline derivative as defined immediately above.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The anti-cell-proliferation defined hereinbefore may be applied as a sole therapy or may involve, in addition to the quinazoline derivative of the invention, conventional radiotherapy or one or more other anti-tumour substances, for example those selected from, for example, mitotic inhibitors, for example vinblastine; alkylating agents, for example cis-platin, carboplatin and cyclophosphamide; antimetabolites, for example 5-fluorouracil, cytosine arabinoside and hydroxyurea, or, for example, one of the preferred antimetabolites disclosed in European Patent Application No. 239362 such as N-{5-[N-(3,4-dihydro-2-methyl-4-oxoquinazolin-6-ylmethyl)-N-methylamino]-2-thenoyl}-

L-glutamic acid; intercalating antibiotics, for example adriamycin and bleomycin; enzymes, for example asparaginase; topoisomerase inhibitors, for example etoposide; biological response modifiers, for example interferon; and anti-hormnones, for example antioestrogens such as 'NOLVADEX' (tamoxifen) or, for example antiandrogens such as 'CASODEX' (4'-cyano-3-(4-fluorophenylsulphonyl)-2-hydroxy-2-methyl-3'-(trifluoromethyl) propionanilide). Such conjoint treatment may be achieved by way of the simultaneous, sequential or separate dosing of the individual components of the treatment. According to this aspect of the invention there is provided a pharmaceutical product comprising a quinazoline derivative of the formula I as defined hereinbefore and an additional anti-tumour substance as defined hereinbefore for the conjoint treatment of cancer.

As stated above the quinazoline derivative defined in the present invention is an effective anti-cancer agent, which property is believed to arise from its Class I receptor tyrosine kinase inhibitory properties. Such a quinazoline derivative of the invention is expected to possess a wide range of anti-cancer properties as Class I receptor tyrosine kinases have been implicated in many common human cancers such as leukemia and breast, lung, colon, rectal, stomach, prostate, bladder, pancreas and ovarian cancer. Thus it is expected that a quinazoline derivative of the invention will possess anti-cancer activity against these cancers. It is in addition expected that a quinazoline derivative of the present invention will possess activity against a range of leukaemias, lymphoid malignancies and solid tumours such as carcinomas and sarcomas in tissues such as the liver, kidney, prostate and pancreas.

It is further expected that a quinazoline derivative of the present invention will possess activity against other cell-proliferation diseases such as psoriasis and benign prostatic hypertrophy (BPH).

It is also to be expected that a quinazoline derivative of the invention will be useful in the treatment of additional disorders of cellular growth in which aberrant cell signalling by way of receptor tyrosine kinase enzymes, including as yet unidentified receptor tyrosine kinase enzymes, are involved. Such disorders include, for example, inflammation, angiogenesis, vascular restenosis, immunological disorders, pancreatitis, kidney disease and blastocyte maturation and implantation.

The invention will now be illustrated in the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multilicities are shown as follows: s, singlet; d, doublet; t, triplet; m, multiplet;

(vii) intermediates were not generally fully characterised and purity was assessed by thin layer chromatography (TLC), infra-red (IR) or NMR analysis;

(viii) the following abbreviations have been used:
DMF N,N-dimethylformamide;
DMA N,N-dimethylacetamide;
NMP N-methylpyrrolidin-2-one;
DMSO dimethylsulphoxide.

EXAMPLE 1

A mixture of 4-chloro-6-(1-imidazolyl)quinazoline (0.35 g) and 3-methylaniline (0.162 ml) in isopropanol (5 ml) was heated at reflux for 1 hour. The mixture was evaporated and the residue was suspended in a mixture of methylene chloride, methanol and triethylamine. The suspension was chromatographed on silica using a mixture of methylene chloride and methanol, increasing in polarity from pure methylene chloride to a 19:1 mixture of methylene chloride: methanol as eluent. There was thus obtained 4-(3-methylanilino)-6-(1-imidazolyl)quinazoline in 39% yield, m.p. 218–232° C.; NMR Spectrum: ($CD_3SOCD_3$) 2.36 (s, 3H), 6.98 (d, 1H), 7.21 (s, 1H), 7.31 (m, 1H), 7.64 (s, 1H), 7.68 (d, 1H), 7.89 (s, 1H), 7.91 (d, 1H), 8.18 (m, 1H), 8.41 (s, 1H), 8.60 (s, 1H), 8.77 (d, 1H); 9.72 (s, 1H), Elemental Analysis: Found C, 70.3; H, 5.1; N, 22.5; $C_{18}H_{15}N_5$ 0.33$H_2O$ requires C, 70.2; H, 5.1; N, 22.7%.

The 4-chloro-6-(1-imidazolyl)quinazoline used as a starting material was prepared as follows:

A mixture of 5-chloro-2-nitrobenzonitrile (20.0 g) and imidazole (22.3 g) in DMA (150 ml) was heated at 140° C. for 6 hours. The mixture was evaporated and the residue was triturated with water to give 5-(1-imidazolyl)-2-nitrobenzonitrile (25.3 g); NMR Spectrum: ($CD_3SOCD_3$) 7.20 (d, 1H), 8.05 (t, 1H), 8.28 (m, 1H), 8.62 (m, 2H), 8.51 (d, 1H);

Elemental Analysis: Found C, 55.5; H, 3.0; N, 27.2; $C_{10}H_6N_4O_2$ requires C, 56.1; H, 2.8; N, 26.2%.

A mixture of 5-(1-imidazolyl)-2-nitrobenzonitrile (2.14 g), hydrazine hydrate (2 ml), ethanol (25 ml) and DMA (10 ml) was stirred and heated to 40° C. Raney nickel (0.6 g) was added in portions whilst maintaining the temperature at 40–50° C. The mixture was stirred at 40–50° C. for 2 hours. The Raney nickel was filtered off, the mixture was evaporated and the residue was triturated with ethyl acetate (10 ml) to give 2-amino-5-(1-imidazolyl)benzamide (2.03 g); NMR Spectrum: ($CD_3SOCD_3$) 6.70 (s, 2H), 6.79 (d, 1H), 7.03 (s, 1H), 7.2 (s, 1H), 7.37 (s, 1H), 7.55 (s, 1H), 7.71 (d, 1H), 7.73 (s, 1H), 8.02 (s, 1H);

Elemental Analysis: Found C, 58.4; H, 6.7; N, 24.4; $C_{10}H_{10}N_4O$ DMA requires C, 58.1; H, 6.6; N, 24.4%.

A mixture of 2-amino-5-(1-imidazolyl)benzamide (12.0 g) and formamide (30 ml) was heated at 160° C. for 3 hours. The mixture was cooled and added to water. The precipitate was filtered off and washed with water to give 6-(1-imidazolyl)-3,4-dihydroquinazolin-4-one (7.5 g); NMR Spectrum: ($CD_3SOCD_3$) 7.15 (s, 1H), 7.80 (s, 1H), 7.90 (s, 1H), 8.13 (m, 2H), 8.26 (d, 1H), 8.41 (s, 1H);

Elemental Analysis: Found C, 55.7; H, 4.1; N, 23.6; $C_{11}H_8N_4O$ 1.3$H_2O$ requires C, 56.0; H, 4.5; N, 23.8%.

6-(1-Imidazolyl)-3,4-dihydroquinazolin-4-one (1.0 g) was dissolved in phosphorus oxychloride (15 ml). DMF (2 drops) was added and the mixture was heated at reflux for 1 hour. The mixture was evaporated, the residue was dissolved in methylene chloride, washed with sodium bicarbonate solution and the organic layer was dried (MgSO$_4$) and evaporated to give 4-chloro-6-(1-imidazolyl)quinazoline (0.36 g) which was used without further purification.

EXAMPLE 2

A mixture of 4-chloro-6-(1-imidazolyl)quinazoline (3.8 g) and 3-chloro-4-fluoroaniline (2.64 g) in isopropanol (50 ml) was heated to reflux for 3 hours. The solid product so obtained was filtered off, washed with isopropanol and with diethyl ether and dried. The solid so obtained was suspended in water (40 ml) and an aqueous ammonium hydroxide solution (15 ml) was added. The mixture was stirred for 10 minutes. the solid was filtered off, washed with 20% aqueous ammonium hydroxide solution, with water, with acetone and with diethyl ether and dried to give 4-(3-chloro-4-fluoroanilino)-6-(1-imidazolyl)quinazoline (1.10 g); NMR Spectrum: (CD$_3$SOCD$_3$) 7.22 (s, 1H), 7.49 (t, 1H), 7.84 (m, 1H), 7.88 (s, 1H), 7.96 (d, 1H), 8.19 (t, 1H), 8.24 (m, 1H), 8.40 (s, 1H), 8.68 (s, 1H), 8.74 (d, 1H), 9.90 (s, 1H);

Elemental Analysis: Found C, 58.0; H, 3.2; N, 19.4; C$_{17}$H$_{11}$N$_5$ClF 0.75H$_2$O requires C, 57.7; H, 3.5; N, 19.8%.

EXAMPLE 3

Sodium hydride (0.24 g) was added to a solution of 2-hydroxypyridine (0.95 g) in NMP (10 ml) and the mixture was stirred at ambient temperature for 30 minutes. A mixture of a portion (3 ml) of the resultant solution and 4-(3,4-dichloroanilino)-6-fluoroquinazoline hydrochloride (0.172 g) was heated at 215° C. for 10 hours. The reaction mixture was acidified with glacial acetic acid and evaporated at 90° C. under high vacuum. The residue was chromatographed on silica using a mixture of methylene chloride and methanol, increasing in polarity from pure methylene chloride to a 19:1 mixture of methylene chloride: methanol as eluent. The product so obtained was triturated with a 1:1 mixture of isopropanol and ethyl acetate. The solid was filtered off, washed with ethyl acetate and dried under high vacuum to give 4-(3,4-dichloroanilino)-6-(2-oxo-1,2-dihydropyridin-1-yl)quinazoline (0.099 g); NMR Spectrum: (CD$_3$SOCD$_3$) 6.44 (m, 1H), 6.57 (m, 1H), 7.55–7.66 (m, 1H), 7.68 (d, 1H), 7.75–8.00 (m, 4H), 8.34 (d, 1H), 8.65 (s, 1H), 8.78 (s, 1H), 9.78 (s, 1H);

Elemental Analysis: Found C, 59.7; H, 3.2; N, 14.4; C$_{19}$H$_{12}$Cl$_2$N$_4$O requires C, 59.7; H, 3.2; N, 14.6%.

The 4-(3,4-dichloroanilino)-6-fluoroquinazoline hydrochloride used as a starting material was prepared as follows:

A mixture of 2-amino-5-fluorobenzoic acid (2.07 g) and formamide (4 ml) was heated at 160° C. for 2 hours, and for a further 2 hours at 180° C. The reaction mixture was allowed to cool and water was added. The reaction product was filtered off and washed with water and with diethyl ether to give 6-fluoro-3,4-dihydroquinazolin-4-one in 78% yield: m.p. 269–271° C.;

Elemental Analysis: Found C, 58.2; H, 3.0; N, 16.9; C$_8$H$_4$N$_2$OF requires C, 58.9; H, 2.5; N, 17.2%.

6-Fluoro-3,4-dihydroquinazolin-4-one (1.0 g) was suspended in a mixture of thionyl chloride (10 ml) and DMF (1to 2 drops). The mixture was heated to reflux for 2 to 3 hours and allowed to cool. Solvent was removed by evaporation and the residue was dried under vacuum to give 4-chloro-6-fluoroquinazoline which was used without further purification.

A mixture of 4-chloro-6-fluoroquinazoline (2 g), 3,4-dichloroaniline (1.78 g) and isopropanol (30 ml) was heated at reflux for 2 hours. The resulting solid was filtered off, washed with isopropanol and with diethyl ether to give 4-(3,4-dichloroanilino)-6-fluoroquinazoline hydrochloride (3.2 g), m.p. >300° C.; NMR Spectrum: (CD$_3$SOCD$_3$) 7.74 (d, 1H), 7.88 (m, 1H), 8.07 (m, 2H), 8.24 (d, 1H), 8.97 (m, 1H), 8.98 (s, 1H);

Elemental Analysis: Found C, 48.7; H, 2.6; N, 12.1; C$_{14}$H$_8$Cl$_2$FN$_3$ 1.0HCl requires C, 48.6; H, 2.6; N, 12.2%.

EXAMPLE 4

A mixture of 4-chloro-6-(1-imidazolyl)quinazoline (0.74 g), 2,4-difluoroaniline (0.61 g) and isopropanol (10 ml) was stirred and heated to reflux for 4 hours. The mixture was cooled to ambient temperature and the solid was isolated and washed in turn with isopropanol and diethyl ether. The solid so obtained was suspended in water (10 ml) and a concentrated aqueous ammonium hydroxide solution (4 ml) was added. The mixture was stirred at ambient temperature for 30 minutes. The mixture was filtered and the solid so obtained was washed in turn with water and with diethyl ether. The solid was purified by column chromatography using a 100:8:1 mixture of methylene chloride, methanol and dilute aqueous ammonium hydroxide as eluent. There was thus obtained 4-(2,4-difluoroanilino)-6-(1-imidazolyl) quinazoline (0.07 g), m.p. 232–234° C.; NMR Spectrum: (CD$_3$SOCD$_3$) 7.15 (m, 1H), 7.2 (s, 1H), 7.4 (m, 1H), 7.6 (m, 1H), 7.85 (s, 1H), 7.9 (d, 1H), 8.2 (m, 1H), 8.38 (s, 1H), 8.5 (s, 1H), 8.7 (d, 1H), 9.8 (broad s,1H);

Elemental Analysis: Found C, 62.6; H, 3.4; N, 21.2; C$_{17}$H$_{11}$F$_2$N$_5$ 0.2H$_2$O requires C, 62.5; H, 3.5; N, 21.4%.

EXAMPLE 5

Using an analogous procedure to that described in Example 4, 4-chloro-6-(1-imidazolyl)quinazoline was reacted with 3,4-difluoroaniline to give 4-(3,4-difluoroanilino)-6-(1-imidazolyl)quinazoline in 35% yield, NMR Spectrum: (CD$_3$SOCD$_3$) 7.2 (s, 1H), 7.4–7.7 (m, 3H), 7.95 (d, 1H), 8.1 (m, 1H), 8.2 (m, 1H), 8.4 (s, 1H), 8.65 (s, 1H), 8.7 (d, 1H), 9.7 (broad s, 1H).

Elemental Analysis: Found C, 62.2; H, 3.6; N, 20.6; C$_{17}$H$_{11}$F$_2$N$_5$ 0.4H$_2$O requires C, 61.7; H, 3.6; N, 21.2%.

EXAMPLE 6

Using an analogous procedure to that described in Example 4, 4-chloro-6-(2-methylimidazol-1-yl)quinazoline was reacted with 3-chloro-4-fluoroaniline to give 4-(3-chloro-4-fluoroanilino)-6-(2-methylimidazol-1-yl) quinazoline in 10% yield: NMR Spectrum: (CD$_3$SOCD$_3$) 2.4 (s, 3H), 7.0 (d, 1H), 7.4 (m, 2H), 7.6 (m, 1H), 7.95 (d, 2H), 8.2 (m, 1H), 8.6 (s, 1H), 8.7 (s, 1H), 9.7 (broad s, 1H).

The 4chloro-6-(2-methylimidazol-1-yl)quinazoline used as a starting material was obtained as follows:

3-Fluorobenzonitrile (25 g) was added dropwise to a stirred mixture of potassium nitrate (21.1 g) and concentrated sulphuric acid (150 ml) which had been cooled in a mixture of salt and ice. The mixture was stirred at ambient temperature for 45 minutes. The mixture was poured onto ice (800 ml) and the precipitate was isolated. The solid so obtained was dissolved in methylene chloride, dried (MgSO$_4$) and the solution was evaporated to give 5-fluoro-2-nitrobenzonitrile (19 g).

A portion (5 g) of the material so obtained was reacted with 2-methylimidazole using an analogous procedure to that described in the first paragraph of the portion of Example 1 which is concerned with the preparation of starting materials. There was thus obtained 5-(2-methylimidazol-1-yl)-2-nitrobenzonitrile in 75% yield.

The material so obtained was used in place of 5-(1-imidazolyl)-2-nitrobenzonitrile as the starting material for the sequence of reactions described in the second, third and fourth paragraphs of the portion of Example 1 which is concerned with the preparation of starting materials. There was thus obtained 4-chloro-6-(2-methylimidazol-1-yl) quinazoline in 54% yield.

EXAMPLE 7

2-Aminoacetaldehyde diethyl acetal (0.2 ml) and triethylamine (0.2 ml) were added in turn to a stirred mixture of 4(3-chloro-4-fluoroanilino)-6-isothiocyanato-7-methoxyquinazoline (0.3 g) and ethanol (5 ml). The mixture was heated to reflux for 1 hour. The mixture was evaporated, 3N aqueous hydrochloric acid (5 ml) was added and the resultant mixture was heated to reflux for 1 hour. The mixture was cooled to ambient temperature and the precipitate was isolated and dried. There was thus obtained 4(3-chloro- 4-fluoroanilino)-7-methoxy-6-(2-thioxo4-imidazolin-1-yl)quinazoline hydrochloride salt (0.32 g), m.p. 226–228° C.; NMR Spectrum: $(CD_3SOCD_3)$ 4.0 (s, 3H), 7.1 (t, 1H), 7.2 (t, 1H), 7.52 (s, 1H), 7.55 (t, 1H), 7.7 (m, 1H), 8.05 (m, 1H), 8.9 (s, 1H), 8.95 (s, 1H), 11.3 (broad s, 1H), 12.5 (broad s, 1H);

Elemental Analysis: Found C, 43.8; H, 4.1; N, 13.8; $C_{18}H_{13}ClFN_5OS$ 1.5HCl 2H$_2$O requires C, 43.9; H, 3.8; N, 14.2%.

The 4-(3-chloro-4-fluoroanilino)-6-isothiocyanato-7-methoxyquinazoline hydrochloride salt used as a starting material was obtained as follows:

Using an analogous procedure to that described in Example 1,4,7-dichloro-6-nitroquinazoline (European Patent Application No. 0635498, within Example 9) was reacted with 3-chloro-4-fluoroaniline to give 7-chloro-4-(3-chloro-4-fluoroanilino)-6-nitroquinazoline in 45% yield.

Sodium methoxide (3.8 g) was added portionwise to a stirred mixture of 7-chloro-4-(3-chloro-4-fluoroanilino)-6-nitroquinazoline (3.5 g) and DMSO (50 ml) which was cooled in an ice-bath. The mixture was stirred at ambient temperature for 3 hours. The mixture was acidified by the addition of glacial acetic acid and then evaporated. The residue was purified by column chromatography using increasingly polar mixtures of methylene chloride and methanol as eluent. There was thus obtained 4-(3-chloro-4-fluoroanilino)-7-methoxy-6-nitroquinazoline (2.9 g).

A mixture of a portion (2.6 g) of the material so obtained, 10% palladium on carbon catalyst (0.35 g), ethanol (120 ml) and DMA (100 ml) was stirred under an atmosphere of hydrogen gas at ambient temperature for 1hour and then at 40° C. for 2 hours. The mixture was filtered and the filtrate was evaporated. The residue was purified by column chromatography using a 19:1 mixture of methylene chloride and methanol as eluent. There was thus obtained 6-amino-4-(3-chloro-4-fluoroanilino)-7-methoxyquinazoline (0.34 g); NMR Spectrum: $(CD_3SOCD_3)$ 3.96 (s, 3H), 5.48 (broad s, 2H), 7.11 (s, 1H), 7.38 (s, 1H), 7.49 (t, 1H), 7.81 (m, 1H), 8.18 (m, 1H), 8.39 (s, 1H), 9.4 (broad s, 1H).

After repetition of the previous steps, thiophosgene (0.5 ml) was added dropwise to a stirred solution of 6-amino4-(3-chloro-4-fluoroanilino)-7-methoxyquinazoline (1.65 g) in 2N aqueous hydrochloric acid (45 ml). The mixture was stirred at ambient temperature for 16 hours. The precipitate was isolated and dried to give 4-(3-chloro-4-fluoroanilino)-6-isothiocyanato-7-methoxyquinazoline which was used without further purification.

EXAMPLE 8

A mixture of 4-(3-chloro-4-fluoroanilino)-7-methoxy-6-(2-thioxo-4-imidazolin-1-yl)quinazoline (0.84 g) and aqueous nitric acid (20%, 20 ml) was stirred and heated until the evolution of nitrogen dioxide was noted. The mixture was heated for a further 15 minutes. The mixture was cooled to ambient temperature and water (20 ml) was added. The mixture was basified by the addition of a concentrated aqueous ammonium hydroxide solution. The resultant mixture was cooled in an ice bath and the resultant precipitate was isolated and dried. There was thus obtained 4-(3-chloro-4-fluoroanilino)-6-(1-imidazolyl)-7-methoxyquinazoline (0.46 g); m.p.233–237° C.; NMR Spectrum: $(CD_3SOCD_3)$ 4.05 (s, 3H), 7.2 (s, iH), 7.5 (m, 2H), 7.65 (s, 1H), 7.9 (m, 1H), 8.1 (s, 1H), 8.25 (m, 1H), 8.65 (s, 1H), 8.7 (s, 1H), 9.9 (broad s, 1H);

Elemental Analysis: Found C, 50.2; H, 4.2; N, 18.1; $C_{18}H_{13}ClFN_5O$ 0.5HNO$_3$ 1.5H$_2$O requires C, 50.5; H, 3.9; N, 18.0%.

EXAMPLE 9

Using an analogous procedure to that described in Example 4,4-chloro-6-(1-imidazolyl)quinazoline was reacted with 4-amino-3-fluorophenyl 2-pyridylmethyl ether to give 4-[2-fluoro-4-(2-pyridylmethoxy)anilino]-6-(1-imidazolyl)quinazoline in 7% yield; NMR Spectrum: $(CD_3SOCD_3)$ 5.23 (s, 2H), 6.95 (m, 1H), 7.1 (m, 1H), 7.2 (s, 1H), 7.38 (m, 1H), 7.44 (t, 1H), 7.58 (d, 1H), 7.83–7.95 (m, 3H), 8.2 (m, 1H), 8.4 (s, 1H), 8.48 (s, 1H), 8.6 (m, 1H), 8.71 (d, 1H), 9.72 (broad s, 1H);

Elemental Analysis: Found C, 65.1; H, 4.1; N, 19.8; $C_{23}H_{17}FN_6O$ 0.75H$_2$O requires C, 64.9; H, 4.4; N, 19.7%.

The 4-amino-3-fluorophenyl 2-pyridylmethyl ether used as a starting material was obtained as follows:

A mixture of 3-fluoro-4-nitrophenol (3.14 g), 2-pyridylmethyl chloride (3.28 g), potassium carbonate (5.52 g) and DMF (20 ml) was stirred at ambient temperature for 16 hours. The mixture was partitioned between ethyl acetate and water. The organic phase was washed with water, dried (MgSO$_4$) and evaporated. The residue was purified by column chromatography using increasingly polar mixtures of hexane and ethyl acetate as eluent to give 3-fluoro-4-nitrophenyl 2-pyridylmethyl ether (0.86 g).

A mixture of the material so obtained, ethyl acetate (25 ml) and 10% pallaidum-on-carbon catalyst (0.08 g) was stirred under an atmosphere of hydrogen gas for 5 hours. The mixture was filtered and evaporated. The residue was purified by column chromatography using increasingly polar mixtures of hexane and ethyl acetate as eluent. There was thus obtained 4-amino-3-fluorophenyl 2-pyridylmethyl ether (0.32 g); NMR Spectrum: $(CD_3SOCD_3)$ 4.6 (broad s, 2H), 5.0 (s, 2H), 6.7 (m, 3H), 7.3 (m, 1H) (d, 1H), 7.8 (m, 1H), 8.6 (d, 1H).

EXAMPLE 10

Using an analogous procedure to that described in Example 4,4-chloro-6-(1-imidazolyl)quinazoline was reacted with 5-amino-2-tolyl 2-pyridylmethyl ether to give 6-(1-imidazolyl)-4[3-methyl4-(2-pyridylmethoxy)anilino]quinazoline in 14% yield, m.p. 208–211° C.; NMR Spectrum: $(CD_3SOCD_3)$ 2.3 (s, 3H), 5.2 (s, 2H), 7.05 (d, 1H), 7.2

(d, 1H), 7.35 (m, 1H), 7.55 (m, 3H), 7.87 (m, 3H), 8.15 (mn, 1H), 8.4 (s, 1H), 8.55 (m, 1H), 8.6 (m, 1H), 8.72 (d, 1H), 9.65 (broad s, 1H);

Elemental Analysis: Found C, 69.7; H, 4.8; N, 20.2; $C_{24}H_{20}N_6O$ 0.25$H_2O$ requires C, 69.8; H, 5.0; N, 20.4%.

The 5-amino-2-tolyl 2-pyridylmethyl ether used as a starting material was obtained as follows:

Sodium hydride (60% dispersion in mineral oil, 1.24 g) was added to a solution of 2-pyridylmethanol (2.49 ml) in NMP (100 ml) and the mixture was stirred at ambient temperature for 15 minutes. 2-Fluoro-5-nitrotoluene (4 g) was added and the mixture was heated to 140° C. for 2.5 hours. The mixture was cooled to ambient temperature, poured into water (300 ml) and stirred for 30 minutes. The precipitate was isolated, washed with water and dried. The material so obtained was purified by column chromatography using increasingly polar mixtures of methylene chloride and methanol as eluent. There was thus obtained 5-nitro-2-tolyl 2-pyridylmethyl ether (1.61 g, 26%); NMR Spectrum: ($CD_3SOCD_3$) 2.32 (s, 3H), 5.35 (s, 2H), 7.21 (d, 1H), 7.35 (m, 1H), (d, 1H), 7.85 (m, 1H), 8.09 (m, 1H), 8.1 (s, 1H), 8.6 (m, 1H).

After repetition of the previous step, a mixture of 5-nitro-2-tolyl 2-pyridylmethyl ether (2 g), iron powder (1 g), concentrated hydrochloric acid (1 ml), water (2 ml) and ethanol (50 ml) was stirred and heated to reflux for 4 hours. The mixture was cooled to ambient temperature, basified by the addition of 2N aqueous sodium hydroxide solution and extracted with methylene chloride. The organic phase was dried ($MgSO_4$) and evaporated. There was thus obtained 5-amino-2-tolyl 2-pyridylmethyl ether in 97% yield. NMR Spectrum: ($CD_3SOCD_3$) 2.09 (s, 3H), 4.61 (s, 2H), 5.0 (s, 2H), 6.32 (m, 1H), 6.42 (d, 1H), 6.67 (d, 1H), 7.31 (m, 1H), 7.50 (d, 1H), 7.81 (m, 1H), 8.54 (m, 1H).

EXAMPLE 11

Using an analogous procedure to that described in Example 4 except that the reaction product was basified by treatment with a saturated aqueous sodium bicarbonate solution rather than with a concentrated aqueous ammonium hydroxide solution, 4-chloro-6-(1-imidazolyl)quinazoline was reacted with 4-amino-2-chlorobenzophenone to give 4-(4-benzoyl-3-chloroanilino)-6-(1-imidazolyl)-quinazoline in 11% yield, m.p. 220–223° C.; NMR Spectrum: ($CD_3SOCD_3$) 7.2 (s, 1H), 7.5–7.8 (m, 6H), 7.9 (s, 1H), 8.0 (d, 1H), (m, 1H), 8.25 (m, 1H), 8.3 (d, 1H), 8.4 (s, 1H), 8.78 (s, 1H), 8.8 (d, 1H), 10.0 (broad s, 1H);

Elemental Analysis: Found C, 66.6; H, 3.8; N, 16.1; $C_{24}H_{16}ClN_5O$ 0.5$H_2O$ requires C, 66.3; H, 3.9; N, 16.1%.

The 4-amino-2-chlorobenzophenone used as a starting material was obtained as follows:

A mixture of 2-chloro-4-nitrobenzoic acid (20 g), thionyl chloride (40 ml) and DMF (5 drops) was stirred and heated to reflux for 1 hour. The mixture was evaporated to give 2-chloro-4-nitrobenzoyl chloride which was used without further purification.

Aluminium chloride (14 g) was added portionwise to a stirred mixture of the 2-chloro-4-nitrobenzoyl chloride so obtained and benzene (50 ml) which had been cooled to 5° C. The mixture was stirred at ambient temperature for 16 hours and then heated to reflux for 1 hour. The mixture was cooled to ambient temperature and added to a vigorously stirred mixture of ice and water. The stirring was continued and concentrated aqueous hydrochloric acid (30 ml) was added. The precipitate was isolated by filtration and dissolved in methylene chloride (250 ml). The organic solution was washed with aqueous sodium hydroxide solution (10%, 2×200 ml) and with brine, dried and evaporated. There was thus obtained 2-chloro-4-nitrobenzophenone as a solid (20 g 77%).

A mixture of a portion (10 g) of the material so obtained, stannous chloride dihydrate (20 g) and concentrated aqueous hydrochloric acid (100 ml) was stirred and heated to reflux for 5 hours. The mixture was cooled to ambient temperature, poured onto a mixture of ice and water and basified by the addition of concentrated aqueous sodium hydroxide solution (30%). The mixture was extracted with diethyl ether and the organic phase was washed with brine, dried and evaporated. The residue was purified by column chromatography using increasingly polar mixtures of hexane and ethyl acetate as eluent. The resultant product was recrystallised from a mixture of hexane and methylene chloride. There was thus obtained 4-amino-2-chlorobenzophenone (2 g); NMR Spectrum: ($CD_3SOCD_3$) 6.0 (s, 2H), 6.6 (m, 1H), 6.7 (d, 1H), 7.1 (d, 1H), 7.5 (m, 2H), 7.7 (m, 3H).

EXAMPLE 12

A mixture of 6-(1-pyrazolyl)-3,4-dihydroquinazoline-4-one (0.32 g), DMF (4 drops) and thionyl chloride (8 ml) was stirred and heated to reflux for 4 hours. The mixture was evaporated. Methylene chloride was added to the residue and the mixture was re-evaporated.

A mixture of the material so obtained, 3-chloro-4-fluoroaniline (0.22 g) and isopropanol (20 ml) was stirred and heated to reflux for 3 hours. The mixture was cooled to ambient temperature, acetone (15 ml) was added and the precipitate was isolated. The material so obtained was purified by column chromatography using a 3:2 mixture of methylene chloride and ethyl acetate as eluent. There were thus obtained in turn: 4-(3-chloro-4-fluoroanilino)-6-(4-chloropyrazol 1-yl)quinazoline (0.047 g), m.p. 225–226° C.; NMR Spectrum: ($CD_3SOCD_3$) 7.46 (t, 1H), 7.85 (m, 1H), 7.94 (d, 1H), 7.99 (s, 1H), (m, 1H), 8.33 (m, 1H), 8.65 (s, 1H), 8.85 (s, 1H), 8.91 (d, 1H), 9.99 (broad s, 1H);

Elemental Analysis: Found C, 54.5; H, 2.7; N, 18.3; $C_{17}H_{10}Cl_2FN_5$ requires C, 54.6; H, 2.7; N, 18.7%; and 4-(3-chloro-4-fluoroanilino)-6-(1-pyrazolyl)quinazoline (0.093 g), m.p. 243–244° C.; NMR Spectrum: ($CD_3SOCD_3$) 6.68 (m, 1H), 7.45 (t, 1H), 7.87 (m, 1H), 7.94 (d, 1H), (m, 1H), 8.39 (m, 1H), 7.87 (m, 1H), 8.61 (d, 1H), 8.63 (s, 1H), 8.91 (d, 1H) s, 1H);

Elemental Analysis: Found C, 59.9; H, 3.2; N, 20.1; $C_{17}H_{11}ClFN_5$ requires C, 60.1; H, 3.3; N, 20.6%.

The 6-(1-pyrazolyl)-3,4-dihydroquinazolin-4-one used as a starting material was obtained as follows:

A mixture of 5-fluoro-2-nitrobenzonitrile (0.166 g), pyrazole (0.272 g), triethylamine (0.55 ml) and DMSO (3 ml) was stirred and heated to 85° C. for 16 hours. The mixture was cooled to ambient temperature and water was added. The precipitate was isolated and purified by column chromatography using methylene chloride as eluent. There was thus obtained 2-nitro-5-(1-pyrazolyl)benzonitrile (0.097 g), m.p. 166–168° C.

Using an analogous procedure to that described in the second paragraph of the portion of Example 1 which is concerned with the preparation of starting materials, 2-nitro-5-(1-pyrazolyl)benzonitrile was reduced with Raney nickel to give 2-amino-5-(1-pyrazolyl)benzamide in 61% yield, m.p. 147–149° C.

A mixture of the material so obtained (1.62 g) and formamide (5 ml) was stirred and heated to 160° C. for 16 hours. The mixture was cooled to ambient temperature and triturated under diethyl ether. The resultant solid was washed in turn with acetone and with ethanol. There was thus obtained 6-(1-pyrazolyl)-3,4-dihydroquinazolin-4-one (1.35 g) which was used without further purification.

EXAMPLE 13

A mixture of 4-chloro-6-(1,2,4-triazol-1-yl)quinazoline (0.54 g), 3-chloro-4-fluoroaniline (0.34 g) and isopropanol (25 ml) was stirred and heated to reflux for 2 hours. The mixture was cooled to ambient temperature, acetone (20 ml) was added and the mixture was filtered. The solid so obtained was washed with acetone and dried to give 4-(3-chloro-4-fluoroanilino)-6-(1,2,4-triazol-1-yl)quinazoline hydrochloride salt (0.61 g), m.p. >250° C.; NMR Spectrum: ($CD_3SOCD_3$) 7.49 (t, 1H), 7.8 (m, 1H), 8.03–8.08 (m, 2H), 8.33 (s, 1H), 8.52 (m, 1H), 8.93 (s, 1H), 9.62 (m, 2H);

Elemental Analysis: Found C, 49.7; H, 2.8; N, 21.9; $C_{16}H_{10}ClFN_6$ 1HCl 10.5$H_2O$ requires C, 49.8; H, 3.1; N, 21.8%.

The 4-chloro-6-(1,2,4-triazol-1-yl)quinazoline used as a starting material was obtained as follows:

A mixture of 5-fluoro-2-nitrobenzonitrile (3 g), 1,2,4-triazole (4.92 g), triethylamine (9.9 ml) and DMSO (50 ml) was stirred and heated to 85° C. for 16 hours. The mixture was cooled to ambient temperature and water was added. The precipitate was isolated and dried to give 2-nitro-5-(1,2,4-triazol-1-yl)benzonitrile (1.9 g) which was used without further purification.

Using an analogous procedure to that described in the second paragraph of the portion of Example 1 which is concerned with the preparation of starting materials, 2-nitro-5-(1,2,4-triazol-1-yl)benzonitrile was reduced with Raney nickel to give 2-amino-5-(1,2,4-triazol-1-yl)benzamide in 83% yield, m.p. 216–218° C.

A mixture of the material so obtained (1.62 g) and formamide (7 ml) was stirred and heated to 160° C. for 16 hours. The mixture was cooled to ambient temperature and acetone was added. The solid was isolated and dried to give 6-(1,2,4-triazol-1-yl)-3,4-dihydroquinazolin-4-one (1.44 g); NMR Spectrum: ($CD_3SOCD_3$) 7.87 (d, 1H), 8.16 (s, 1H), 8.3 (s, 1H), 8.33 (m, 1H), 8.54 (d, 1H), 9.5 (s, 1H), 12.45 (broad s, 1H).

A mixture of a portion (0.5 g) of the material so obtained, DMF (4 drops) and thionyl chloride (10 ml) was stirred and heated to reflux for 3 hours. The mixture was evaporated, methylene chloride was added to the residue and the mixture was re-evaporated. There was thus obtained 4-chloro-6-(1,2,4-triazol-1-yl)quinazoline (0.54 g) which was used without further purification.

EXAMPLE 14

Using an analogous procedure to that described in Example 13 except that the reaction product was purified by column chromatography using a 100:8:1 mixture of methylene chloride, methanol and a dilute aqueous ammonium hydroxide solution, 4-chloro-6-(1,2,4-triazol-1-yl) quinazoline was reacted with 2,4-difluoroaniline to give 4-(2,4-difluoroanilino)-6-(1,2,4-triazol-1-yl)quinazoline in 30% yield, m.p. >250° C.; NMR Spectrum: ($CD_3SOCD_3$) 7.18 (m, 1H), 7.4 (m, 1H), 7.6 (m, 1H), 7.98 (d, 1H), 8.38 (m, 2H), 8.53 (s, 1H), 8.96 (d, 1H), 9.37 (s, 1H), 10.0 (broad s, 1H);

Elemental Analysis: Found C, 58.3; H, 3.2; N, 25.2; $C_{16}H_{10}F_2N_6$ 0.3$H_2O$ requires C, 58.3; H, 3.2; N, 25.5%.

EXAMPLE 15

A mixture of 6-fluoro-4-(3-methylanilino)quinazoline hydrochloride salt (0.347 g), benzimidazole (0.33 g), potassium carbonate (0.78 g) and DMF (7 ml) was stirred and heated at 150° C. for 24 hours. The mixture was evaporated and the residue was suspended in a mixture of methylene chloride and methanol. The suspension was filtered and the filtrate was evaporated to give a solid which was washed with ethyl acetate and purified by column chromatography using a 24:1 mixture of methylene chloride and methanol as eluent. The resultant solid was triturated with methylene chloride, filtered and dried to give 6-(1-benzimidazolyl)-4-(3-methylanilino)quinazoline (0.2 g), m.p. 245–246° C.; NMR Spectrum: ($CD_3SOCD_3$) 2.35 (s, 3H), 6.96–6.99 (d, 1H), 7.27–7.33 (t, 1H), 7.35–7.42 (m, 2H), 7.64–7.77 (m, 3H), 7.82–7.86 (m, 1H), 7.99–8.03 (d, 1H), 8.15–8.20 (m, 1H), 8.66 (s, 2H), 8.90 (d, 1H), 9.80 (s, 1H);

Elemental Analysis: Found C, 72.8; H, 5.0; N, 19.3; $C_{22}H_{17}N_5$ 0.6$H_2O$ requires C, 73.0; H, 5.1; N, 19.3%.

The 6-fluoro-4-(3-methylanilino)quinazoline used as a starting material was obtained as follows:

4-Chloro-6-fluoroquinazoline (1.1 g) was suspended in isopropanol (20 ml) and 3-methylaniline (0.65 ml) was added. The mixture was heated to reflux for 2 hours. The reaction mixture was allowed to cool and the precipitate was filtered off. The solid so obtained was suspended in 2N aqueous hydrochloric acid and stirred for several minutes. The mixture was filtered to give 6-fluoro-4-(3-methylanilino)quinazoline hydrochloride salt in 43% yield, m.p. 255–260° C.;

Elemental Analysis: Found C, 57.1; H, 4.6; N, 13.2; $C_{15}H_{13}N_3F$ 1.67HCl requires C, 57.4; H. 4.7; N, 13.4%;

EXAMPLE 16

The following illustrate representative pharmaceutical dosage forms containing the compound of formula I, or a pharmaceutically-acceptable salt thereof (hereafter compound X), for therapeutic or prophylactic use in humans:

| (a) | Tablet I | mg/tablet |
|---|---|---|
| | Compound X | 100 |
| | Lactose Ph. Eur. | 182.75 |
| | Croscarmellose sodium | 12.0 |
| | Maize starch paste (5% w/v paste) | 2.25 |
| | Magnesium stearate | 3.0 |

| (b) | Tablet II | mg/tablet |
|---|---|---|
| | Compound X | 50 |
| | Lactose Ph. Eur. | 223.75 |
| | Croscarmellose sodium | 6.0 |
| | Maize starch | 15.0 |
| | Polyvinylpyrrolidone | 2.25 |
| | Magnesium stearate | 3.0 |

| (c) | Tablet III | mg/tablet |
|---|---|---|
| | Compound X | 1.0 |
| | Lactose Ph. Eur. | 93.25 |
| | Croscarmellose sodium | 4.0 |
| | Maize starch paste (5% w/v paste) | 0.75 |
| | Magnesium stearate | 1.0 |

| (d) | Capsule | mg/capsule |
|---|---|---|
| | Compound X | 10 |
| | Lactose Ph. Eur. | 488.5 |
| | Magnesium stearate | 1.5 |
| (e) | Injection I | (50 mg/ml) |
| | Compound X | 5.0% w/v |
| | 1M Sodium hydroxide solution | 15.0% w/v |
| | 0.1M Hydrochloric acid | |
| | (to adjust pH to 7.6) | |
| | Polyethylene glycol 400 | 4.5% w/v |
| | Water for injection to 100% | |
| (f) | Injection II | (10 mg/ml) |
| | Compound X | 1.0% w/v |
| | Sodium phosphate BP | 3.6% w/v |
| | 0.1M Sodium hydroxide solution | 15.0% v/v |
| | Water for injection to 100% | |
| (g) | Injection III | (1 mg/ml, buffered to pH6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

Note
The above formulations may be obtained by conventional procedures well known in the pharmaceutical art. The tablets (a)–(c) may be enteric coated by conventional means, for example to provide a coating of cellulose acetate phthalate.

I claim:
1. A quinazoline derivative of the formula I

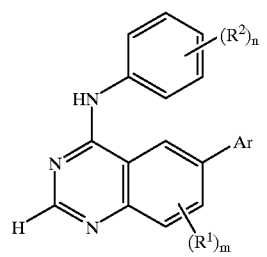

I wherein m is 1 or 2;
each $R^1$ is independently hydrogen, halogeno, cyano, amino, nitro, carbamoyl, carboxy, (1–4C) alkoxycarbonyl, (1–4C)alkyl, (1–4C)alkylthio, (1–4C) alkylamino, di-[1–4C)alkyl]amino, (2–4C) alkanoylamino or (1–4C)alkoxy;
n is 1, 2 or 3;
each $R^2$ is independently hydrogen, hydroxy, halogeno, trifluoromethyl, trifluoromethoxy, amino, nitro, cyano, (1–4C)alkyl, (1–4C)alkoxy, (1–4C)alkylamino, di-[(1–4C)alkyl]amino, (1–4C)alkylthio, (1–4C) alkylsulphinyl, (1–4C)alkylsulphonyl, (2–4C) alkanoylamino, (2–4C)alkanoyl or (1–3C) alkylenedioxy, or $R^2$ is a group of the formula —X—Q which is located para to the NH group in formula I and wherein X is a group of the formula CO, $C(R^3)_2$, $CH(OR^3)$, $C(R^3)_2$—$C(R^3)_2$, $C(R^3)$=$C(R^3)$, C≡C, CH(CN), O, S, SO, $SO_2$, $CONR^3$, $SO_2NR^3$, $NR^3CO$, $NR^3SO_2$, $OC(R^3)_2$, $SC(R^3)_2$, $C(R^3)_2O$ or $C(R^3)_2S$ wherein each $R^3$ is independently hydrogen or (1–4C) alkyl, and Q is a phenyl or naphthyl group or a 5- or 6-membered heteroaryl moiety containing up to three heteroatoms selected from oxygen, nitrogen and sulphur, which heteroaryl moiety is a single ring or is fused to a benzo ring and wherein said phenyl or naphthyl group or heteroaryl moiety is optionally substituted with one, two or three substituents selected from halogeno, trifluoromethyl, cyano, carbamoyl, hydroxy, amino, nitro, (1–4C)alkyl, (1–4C)alkoxy, (1–4C)alkylamino, di-[(1–4C)alkyl]amino, (2–4C) alkanoylamino, N-(1–4C)alkylcarbamoyl and N,N-di-[(1–4C)alkyl]carbamoyl; and
Ar is a 5- or 9-membered nitrogen-linked heteroaryl moiety containing up to four nitrogen heteroatoms,
or Ar is 2-oxo-4-imidazolin-1-yl, 2-oxo-1,2-dihydrolpyridin-1-yl, 4-oxo-1,4-dihydropyridin-1-yl, 2-oxo-1,2-dihydropyrimidin-1-yl, 4-oxo-3 4-dihydropyrimidin-3-yl, 2,4-dioxo-1,2,3,4-tetrahydropyrimidin-1-yl, 2-oxo-1,2-dihydropyrazin-1-yl, 2,3-dioxo-1,2,3,4-tetrahydropyrazin-1-yl, 3-oxo-2,3-dihydropyridazin-2-yl or 3,6-dioxo-1,2,3,6-tetrahydropyridazin-1-yl or the corresponding thioxo analogues thereof, or 2-oxoindolin-1-yl, 2,3-dioxoindolin-1-yl, 2-oxo-2,3-dihydrobenzimidazol-1-yl, 3-oxo-2,3-dihydro-1H-indazol-1-yl, 3-oxo-2,3-dihydro-1H-indazol-2-yl, 2-oxo-1,2-dihydroquinolin-1-yl, 2-oxo-1,2,3,4-tetrahydroquinolin-1-yl, 1-oxo-1,2-dihydroisoquinolin-2-yl, 2-oxo-1,2-dihydroquinazolin-1-yl, 2,4-dioxo-1,2,3,4-tetrahydroquinazolin-1-yl, 2-oxo-1,2-dihydroquinoxalin-1-yl, 2,3-dioxo-1,2,3,4-tetrahydroquinoxalin-1-yl, 4-oxo-1,4-dihydrocinnolin-1-yl, 3,4-dioxo-1,2,3,4-tetrahydrocinnolin-1-yl or 3,4-dioxo-1,2,3,4-tetrahydrocinnolin-2-yl or the corresponding thioxo analogues thereof, and Ar is optionally substituted with one, two or three substituents selected from halogeno, hydroxy, amino, mercapto, carboxy, carbamoyl, (1–4C)alkyl, (1–4C) alkoxy, (1–4C)alkylamino, di-[(1–4C)alkyl]amino, (1–4C)alkylthio, (2–4C)alkanoyl, (1–4C) alkoxycarbonyl, (2–4C)alkanoylamino, N-(1–4C) alkylcarbamoyl, N,N-di-[(1–4C)alkyl]carbamoyl, N-[hydroxy-(2–4C)alkyl]carbamoyl, N,N-di-[hydroxy-(2–4C)alkyl]carbamoyl, N-[(1–4C)alkoxy-(2–4C)alkyl]carbamoyl, N,N-di-[(1–4C)alkoxy-(2–4C)alkyl]carbamoyl, amino-(1–4C)alkyl, (1–4C) alkylamino-(1–4C)alkyl di-[(1–4C)alkyl]amino-(1–4C)alkyl, pyrrolidin-1-yl-(1–4C)alkyl, piperidino-(1–4C)alkyl morpholino-(1–4C)alkyl, piperazin-1-yl-(1–4C)alkyl and 4-(1–4C)alkylpiperazin-1-yl-(1–4C) alkyl;
or pharmaceutically-acceptable salt thereof.
2. A quinazoline derivative of the formula I as claimed in claim 1 wherein m is 1 or 2;
each $R^1$ is independently hydrogen, halogeno, cyano, amino, nitro, carbamoyl, carboxy, (1–4C) alkoxycarbonyl, (1–4C)alkyl, (1–4C)alkylthio, (1–4C) alkylamino, di-[(1–4C)alkyl]amino, (2–4C) alkanoylamino or (1–4C)alkoxy;
n is 1, 2 or 3;
each $R^2$ is independently hydrogen, hydroxy, halogeno, trifluoromethyl, trifluoromethoxy, amino, nitro, cyano, (1–4C)alkyl, (1–4C)alkoxy, (1–4C)alkylamino, di-[(1–4C)alkyl]amino, (1–4C)alkylthio, (1–4C) alkylsulphinyl, (1–4C)alkylsulphonyl, (2–4C) alkanoylamino, (2–4C)alkanoyl or, (1–3C) alkylenedioxy; and
Ar is a 5- or 9-membered nitrogen-linked heteroaryl moiety containing up to four nitrogen heteroatoms;

or Ar is 2-oxo-1,2-dihydrolpyridin-1-yl, 4-oxo-1,4-dihydropyridin-1-yl, 2-oxo-1,2-dihydropyrimidin-1-yl, 4-oxo-3,4-dihydropyrimidin-3-yl, 2,4-dioxo-1,2,3,4-tetrahydropyrimidin-1-yl, 2-oxo-1,2-dihydropyrazin-1-yl, 2,3-dioxo-1,2,3,4-tetrahydropyrazin-1-yl, 3-oxo-2,3-dihydropyridazin-2-yl or 3,6-dioxo-1,2,3,6-tetrahydropyridazin-1-yl or the corresponding thioxo analogues thereof, or 2-oxoindolin-1-yl, 2,3-dioxoindolin-1-yl, 2-oxo-2,3-dihydrobenzimidazol-1-yl, 3-oxo-2,3-dihydro-1H-indazol-1-yl, 3-oxo-2,3-dihydro-1H-indazol-2-yl, 2-oxo-1,2-dihydroquinolin-1-yl, 2-oxo-1,2,3,4-tetrahydroquinolin-1-yl, 1-oxo-1,2-dihydroisoquinolin-2-yl, 2-oxo-1,2-dihydroquinazolin-1-yl, 2,4-dioxo-1,2,3,4-tetrahydroquinazolin-1-yl, 2-oxo-1,2-dihydroquinoxalin-1-yl, 2,3-dioxo-1,2,3,4-tetrahydroquinoxalin-1-yl, 4-oxo-1,4-dihydrocinnolin-1-yl, 3,4-dioxo-1,2,3,4-tetrahydrocinnolin-1-yl or 3,4-dioxo-1,2,3,4-tetrahydrocinnolin-2-yl or the corresponding thioxo analogues thereof, and Ar may optionally bear up to three substituents selected from halogeno, hydroxy, amino, mercapto, carboxy, carbamoyl, (1–4C)alkyl, (1–4C)alkoxy, (1–4C)alkylamino, di-[(1–4C)alkyl]amino, (1–4C)alkylthio, (2–4C)alkanoyl, (1–4C)alkoxycarbonyl, N-(1–4C)alkylcarbamoyl, N,N-di-[(1–4C)alkyl]carbamoyl, N-[hydroxy-(1–4C)alkyl]carbamoyl, N,N-di-[hydroxy-(1–4C)alkyl]-carbamoyl, N-[(1–4C)alkoxy-(1–4C)alkyl]carbamoyl and N,N-di-[(1–4C)alkoxy-(1–4C)alkyl]carbamoyl;

or a pharmaceutically-acceptable salt thereof.

3. A quinazoline derivative of the formula I as claimed in claim 1 wherein m is 1 and $R^1$ is hydrogen, 7-fluoro, 7-chloro or 7-methoxy;

n is 1 or 2 and each $R^2$ is independently fluoro, chloro, bromo, methyl and ethyl, or one $R^2$ is a group of the formula —X—Q which is located para to the NH group in formula I and wherein X is a group of formula CO or $OCH_2$ and Q is phenyl or 2-pyridyl; and Ar is 1-pyrazoyl, 1-imidazolyl, 1,2,4-triazol-1-yl or 1-benzimidazolyl which optionally bears a substituent selected from fluoro, chloro, bromo, methyl and ethyl;

or a pharmaceutically-acceptable salt thereof.

4. A quinazoline derivative of the formula I as claimed in claim 1 wherein m is 1 and $R^1$ is hydrogen, 7-fluoro, 7-chloro or 7-methoxy;

n is 1 or 2 and each $R^2$ independently fluoro, chloro, bromo, methyl and ethyl, or one $R^2$ is a group off the formula —X—Q which is located para to the NH group in formula I and wherein X is a group of formula CO or $OCH_2$, and Q is phenyl or 2-pyridyl; and Ar is 2-oxo-1,2-dihydropyridin-1-yl, or a pharmaceutically-acceptable acid-additional salt thereof.

5. A quinazoline derivative of the formula I as claimed in claim 1 wherein $(R^1)_m$ is hydrogen or 7-methoxy;

$(R^2)_n$ is 3-chloro-4-fluoro, 3,4-dichloro, 2,4-difluoro, 3,4-difluoro, 3-methyl, 2-fluoro-4-(2-pyridylmethoxy), 3-methyl-4-(2-pyridylmethoxy) or 4-benzoyl-3-chloro and Ar is 1-imidazolyl, 1-benzimidazolyl, 1-pyrazolyl 1,2,4-triazol-1-yl or 2-oxo-1,2-dihydropyridin-1-yl;

or a pharmaceutically-acceptable acid-addition salt thereof.

6. A quinazoline derivative of the formula I as claimed in claim 1 selected from:

4-(3-methylanilino)-6-(1-imidazolyl)quinazoline and 4-(3-chloro-4-fluoroanilino)-6-(1-imidazolyl)quinazoline, or a pharmaceutically-acceptable salt thereof.

7. A quinazoline derivative of the formula I as claimed in claim 1 selected from:

6-(1-imidazolyl)-4-[3-methyl-4-(2-pyridylmethoxy)anilino]quinazoline and 4-(4-benzoyl-3-chloroanilino)-6-(1-imidazolyl)quinazoline;

or a pharmaceutically-acceptable acid-addition salt thereof.

8. A process for the preparation of a quinazoline derivative of the formula I, or a pharmaceutically-acceptable salt thereof, as claimed in claimed in 1 which comprises:

(a) the reaction of a quinazoline of the formula II

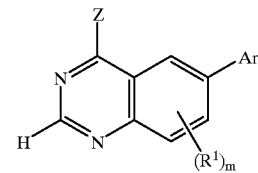

II wherein Z is a leaving group, with an aniline of the formula III

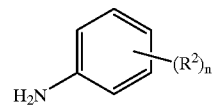

III or (b) the reaction, of a quinazoline of the formula IV

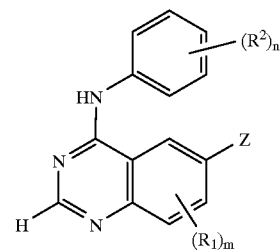

IV wherein Z is a leaving group, with a group of the formula Ar—H where Ar is as defined in claim 1.

9. A pharmaceutical composition which comprises a pharmaceutically effective amount of a quinazoline derivative of the formula I as claimed in claim 1, or a pharmaceutically-acceptable salt thereof, in association with a pharmaceutically-acceptable diluent or carrier.

10. A method for producing an anti-cell-proliferation effect in a warm-blooded animal in need thereof, which method comprises administering to said animal an anti-cell-proliferation effective amount of a quinazoline derivative as claimed in claim 1.

* * * * *